United States Patent [19]
Grote et al.

[11] Patent Number: 5,099,020
[45] Date of Patent: Mar. 24, 1992

[54] BARBITURATE ASSAY COMPOSITIONS AND METHODS

[75] Inventors: Jonathan Grote, Grayslake; Hsiang Hu, Libertyville, both of Ill.

[73] Assignee: Abbott Laboratories, Abbott Park, Ill.

[21] Appl. No.: 544,432

[22] Filed: Jun. 27, 1990

Related U.S. Application Data

[62] Division of Ser. No. 441,956, Nov. 27, 1989.

[51] Int. Cl.$^5$ ........................................ C07D 239/545
[52] U.S. Cl. .................................... 530/363; 544/299; 544/302; 544/305; 544/306; 544/229; 544/300; 436/500; 436/537; 436/546; 530/362; 530/363; 530/367; 530/386; 530/389.8; 530/812; 530/391.9
[58] Field of Search ............... 544/299, 300, 302, 305, 544/306, 229; 436/500, 537, 546; 530/362, 812, 363, 367, 386, 387

[56] References Cited

U.S. PATENT DOCUMENTS

| | | | |
|---|---|---|---|
| 3,766,162 | 10/1973 | Spector | 260/112 R |
| 3,905,871 | 9/1975 | Rubenstein | 195/63 |
| 3,923,995 | 12/1975 | Samour | 424/273 |
| 4,107,157 | 8/1978 | Spector | 424/1 |
| 4,244,939 | 1/1981 | Parsons, Jr. et al. | 544/301 |
| 4,255,329 | 3/1981 | Ullman | 544/299 |
| 4,269,511 | 5/1981 | Erwin | 536/368 |
| 4,351,760 | 9/1982 | Khanna et al. | 435/7 |
| 4,420,568 | 12/1983 | Wang et al. | 436/536 |
| 4,476,228 | 10/1984 | Huchzermeier et al. | 436/500 |
| 4,476,229 | 10/1984 | Fino et al. | 436/500 |
| 4,481,136 | 11/1984 | Khanna et al. | 436/546 |
| 4,492,762 | 1/1985 | Wang et al. | 436/537 |
| 4,510,251 | 4/1985 | Kirkemo et al. | 436/536 |
| 4,585,862 | 4/1986 | Wang et al. | 544/319 |
| 4,588,697 | 5/1986 | Khanna et al. | 436/518 |
| 4,593,089 | 6/1986 | Wang et al. | 436/536 |
| 4,614,823 | 9/1986 | Kirkemo et al. | 544/300 |
| 4,668,640 | 5/1987 | Wang et al. | 436/536 |
| 4,681,859 | 7/1988 | Kramer | 436/501 |

FOREIGN PATENT DOCUMENTS

2111476-A 7/1983 United Kingdom.

OTHER PUBLICATIONS

Journal of Chromatography, 220 (1981) 253–274, "Analysis of Barbiturates by Gas Chromatography".
Analytical Biochemistry 162, 89–101 (1987), "4'-[Aminomethyl]fluorescein and Its N-Alkyl Derivatives: Useful Reagents in Immunodiagnostic Techniques".
Clinical Chemistry 30/2, 307–308 (1984) "Rapid Quantification of Pentobarbital in Serum by Fluorescence Polarization Immunoassay".
Journal of Immunological Methods, 28 (1979) 51–47 "Determination of Phenobarbital by Radiomimmunoassay".
Abstract—98:191179w "Antibodies to Seconal and their Use Forquantitative Barbiturate Determination" Pharmacology, vol. 98, 1983, p. 9.
Abstract of Clinical Chemistry (Winston-Salem, N.C.) Abstract—102:1481u "Single-Reagent Polarization Fluoroimmunoassay for Barbiturates in Urine".
Therapeutic Drug Monitoring, 4:397–403, 1982 "Direct Determination of Phenobarbital in Serum or Plasma by Polarization Fluoroimmunoassay".
Clinical Chemistry, 33/10, 1921–1923 (1987) "Multiple Drugs of Abuse in Urine Detected with a Single Reagent and Fluorescence Polarization".
Clinical Chemistry, 30/11, 1976–1769 (1984) "Single-Reagent Polarization Fluoroimmunoassay for Barbiturates in Urine".
Hackh's Chemical Dictionary, 3rd Ed., J. Grant, pp. 43 & 166.

*Primary Examiner*—Cecilia Shen
*Attorney, Agent, or Firm*—Roberta L. Hastreiter; Thomas M. Breininger

[57]. ABSTRACT

The present invention provides methods and compositions for assaying biological samples, such as human serum, for barbiturates. In one aspect, analogs of barbiturates derivatized with fluorescein and analogs of barbiturates derivatized with immunogenic polypeptides are provided. The fluorescent analogs are employed as tracers in a competitive homogeneous immunoassay, i.e., a fluorescence polarization immunoassay, for detecting barbiturates. The immunogenic analogs are employed to make anti-barbiturate antiserum of the invention for use in the immunoassay method. Intermediates for preparing the fluorescent and immunogenic analogs are also provided. Further provided are test kits, comprising a fluorescent tracer and an antiserum according to the invention, for analyzing biological samples by fluorescence polarization immunoassay for the presence of a barbiturate. Further, an improvement is provided in immunoassays for analytes in serum, wherein a transfer means, such as a pipette, is used repeatedly to transfer different samples into the assay system. In the improvement, an aqueous solution of specified composition, comprising dimethylsulfoxide and an alkali halide, is used to wash the transfer means between transfers.

14 Claims, No Drawings

BARBITURATE ASSAY COMPOSITIONS AND METHODS

This is a division of application Ser. No. 07/441,956, filed Nov. 27, 1989.

TECHNICAL FIELD

The present invention relates to immunoassays and, more particularly, to novel compounds and antisera for use in fluorescence polarization immunoassays for barbiturates, novel methods of using the compounds and antisera, and novel intermediates for making the compounds and antisera.

The invention also concerns an improvement in immunoassays for analytes in serum samples.

BACKGROUND OF THE INVENTION

The barbiturates are a class of synthetic drugs commonly prescribed as sedatives, hypnotics, and anticonvulsants. These drugs produce depression of the central nervous system ranging from mild sedation to coma. The degree of depression depends upon the type of barbiturate, the amount consumed, the method of administration of the barbiturate, and the state of excitability of the nervous system of the individual taking the drug. Excessive use of barbiturates may lead to habituation or addiction. Overdose on, or abrupt withdrawal from, barbiturates can cause coma or even death.

Even though the legal availability of barbiturates has decreased, use and, sometimes, abuse of barbiturates continues.

Detection of barbiturates in a person's system is helpful in confirming a diagnosis of barbiturate use or overdose and selecting an appropriate treatment.

The types of biological samples used for detecting barbiturates include urine, serum, plasma, and tissue. Barbiturates have been detected by a number of techniques, including thin-layer chromatography (TLC), gas chromatography (GC), and high performance liquid chromatography (HPLC). These methods generally involve chemical extractions of the drugs, and are complicated, labor-intensive procedures requiring highly trained personnel and lengthly assay times. In addition, TLC lacks sensitivity, and GC often requires derivatization of the drug prior to assay.

In general, competitive immunoassays have provided a preferable alternative to methods such as TLC, GC, and HPLC in assaying of biological samples for barbiturates. Among these competitive binding immunoassays is fluorescence polarization immunoassay.

Typically, competitive immunoassays (sometimes referred to as "competitive binding immunoassays") are used for detecting the presence or measuring the concentration of a ligand analyte in a test sample. The ligand analyte competes with a labeled reagent, which is an analog of the analyte and sometimes referred to as a "tracer," for a limited number of receptor sites on antibodies specific to the analyte and the analog. The concentration of ligand analyte in a sample determines the amount of the analog (tracer) which binds to the antibody in a competitive immunoassay of a sample. In particular, the amount of analog that will bind to the antibody is inversely proportional to the concentration of analyte in the sample being assayed, because the analyte and the analog each bind to the antibody in proportion to their respective concentrations.

In an homogeneous competitive binding assay, such as a fluorescence polarization immunoassay, antibody, together with analyte (ligand whose presence or concentration is to be determined in the assay) and ligand analog (an analog of the analyte which, like the analyte, is capable of binding to the antibody with an affinity approximately the same as that of the analyte) are all present in solution (homogeneous phase). By contrast, in an heterogeneous competitive binding assay, the antibody is typically bound to a solid phase, while analyte and analyte analog are present in a solution in contact with the solid phase.

Fluorescence polarization provides a means for measuring the amount of tracer-antibody conjugate produced in an homogeneous competitive binding immunoassay. Fluorescence polarization techniques are based on the principle that a fluorescently labeled tracer, when excited by plane-polarized light, will emit fluorescence having a degree of polarization inversely related to the rate of rotation of the tracer. Accordingly, when a tracer-antibody conjugate having a fluorescent label as part of the tracer, particularly when the tracer has a molecular weight much smaller than that of the antibody, is excited with plane-polarized light, the emitted light, due to fluorescence emission, remains highly polarized because the fluorophore, bound to the relatively massive and slowly rotating antibody, is constrained from rotating very far between the time that light is absorbed and fluorescence emission occurs. In contrast, when an unbound tracer molecule is excited by plane-polarized light, its rotation is much faster than the corresponding tracer-antibody conjugate so that the orientations of a population of excited, unbound tracers approaches randomization much more quickly than that of a population of antibody-bound tracers and, as a result, the fluorescence emission from unbound tracer is closer to completely depolarized than that from antibody-bound tracer. Consequently, in fluorescence polarization immunoassay of a set of samples with different concentrations of analyte, but a constant concentration of antibody and tracer, the observed polarization of fluorescence will decrease with increasing concentration of analyte.

In a fluorescence polarization immunoassay ("FPIA"), being an homogeneous assay, final polarization readings are taken from a solution in which both free tracer and tracer bound to antibody are present. Thus, the need to separate free from bound tracer, a need that exists in many other immunoassay methods, is advantageously obviated in FPIA.

By using standard preparations (constant amounts of antibody and tracer, constant volume of solution, constant pH, ionic strength, temperature and the like) both for a plurality of samples of known and different concentrations of analyte ("calibrators") and for samples with unknown quantities of analyte, FPIA provides a means for quantitatively measuring the amount of tracer-antibody complex formed in an homogeneous competitive binding immunoassay with a test sample (i.e., an unknown). This procedure is currently employed in the art, such as with the TDx ® Therapeutic Drug Monitoring System, which is commercially available from Abbott Laboratories, Inc. (Irving, Tex., U.S.A.). The TDx system is described, for example, in U.S. Pat. Nos. 4,420,568 and 4,269,511, which are incorporated herein by reference.

In an FPIA system, employing standard preparations for calibration solutions and test samples, when the analyte employed in the calibrator solutions is chemically the same as that in test samples (unknowns) being assayed, or when the affinities of the antibody for the analyte in the calibrators and the analyte in the test samples being assayed are known, FPIA also provides a means for quantitatively measuring the concentration of analyte in the test samples. When the analyte in a test sample is a complex mixture of chemically related compounds, and (as it usually will be) the analyte in the calibrators is a single, well defined compound, FPIA can be used to discriminate between a test sample which has analyte (above a certain minimum amount (sensitivity)) and a test sample which does not have analyte (above the sensitivity level) but can provide at best only a qualitative measure of the concentration of analyte in a test sample.

An accurate and reliable immunoassay for barbiturates requires that cross-reactivity of antibody with compounds other than the intended analyte be minimized. Drugs that are structurally similar to barbiturates, such as phenytoin, p-hydroxyphenytoin, glutethimide, and primidone are commonly recognized interferences (undesirable cross-reactants) in competitive barbiturate assays. Having antisera and tracers for use in an FPIA for barbiturates that would minimize cross-reactivity with such interferences would be advantageous.

Furthermore, it would be desirable to prepare tracers, for use in FPIA's for barbiturates, by methods which do not employ compositions that are considered "controlled substances" subject to regulation by the United States Drug Enforcement Agency (DEA). Avoiding use of such compounds would eliminate the need for the significant time, effort and expense required to comply with DEA regulations involving controlled substances.

Finally, a barbiturate assay method, which would require no pretreatment of specimen before analysis thereof, would be desirable because it would be more rapid and less prone to error than methods which do require such pretreatment.

For prior art relating to the detection of barbiturates in biological samples, see U.S. Pat. No. 4,244,939 (barbituric acid tracers and their preparation), U.S. Pat. No. 4,107,157 (barbituric acid antigens and antibodies specific therefore), U.S. Pat. No. 3,766,162 (barbituric acid antigens and antibodies specific therefore), U.S. Pat. No. 3,905,871 (lactam conjugates to enzymes), U.S. Pat. No. 3,875,011 (enzyme immunoassays with glucose-6-phosphate dehydrogenase), Clinical Chemistry 1987, 33, 1921 (polarization fluoroimmunoassay for drugs of abuse), Clinical Chemistry 1984, 30, 1765 (polarization fluoroimmunoassay for barbiturates), Clin. Chem. 1984, 30, 307 (phenobarbital determination in serum by polarization fluoroimmunoassay), and Therapeutic Drug Monitoring 1982, 4, 397 (phenobarbital determination in serum by polarization fluoroimmunoassay). See also commonly assigned U.S. patent application Ser. No. 284,781, filed Dec. 12, 1988, which is also incorporated herein by reference.

Fluorescein analogs derivatized with primary or secondary amino groups, through which the analogs can be used to prepare analyte analogs useful as tracers in FPIA's, are known. Among these are fluorescein amine I (5-aminofluorescein), fluorescein amine II (6-aminofluorescein), 4'-aminomethylfluorescein, and 4'-(substituted amino)methyl fluoresceins. In this regard, see Anal. Biochem. (1987) 162, 89 (1987) and U.S. Pat. Nos. 4,614,823 and 4,510,251, all of which are incorporated herein by reference.

SUMMARY OF THE INVENTION

The present invention provides compositions and methods for immunoassay of barbiturates in biological samples, such as samples of serum, urine and plasma, and immunoassays generally in serum.

With respect to barbiturates, the invention provides compositions and methods for detecting the presence and approximate quantity of a wide variety of barbiturates, singly or in combination, in biological samples using FPIA.

The FPIA method provided by the invention entails, in its preferred application to analysis of human serum samples, incubation of a sample of human serum to be tested for barbiturates with (1) an aliquot of a novel antiserum of the invention, which is prepared with a novel immunogen of the invention and which, surprisingly, has significant cross-reactivity with a wide variety of barbiturates but low cross-reactivity with many common interferants in assays for barbiturates, and (2) a novel, fluorescent tracer according to the invention.

The immunogens and tracers of the invention can be provided by synthetic methods, which avoid the use of substances controlled by the U.S. DEA. The invention also facilitates such synthetic methods by providing novel barbiturate derivatives, which are advantageously employed as intermediates in the syntheses of tracers and immunogens of the invention.

An FPIA of barbiturates in accordance with the invention requires no pretreatment of sample and, consequently, is more rapid and accurate than other barbiturate assay methods.

Advantageously and unexpectedly, in an FPIA of barbirurates in accordance with the invention, interferants from many compounds, which have plagued other assays for barbiturates, are reduced to insignificant levels. For example, phenytoin and primidone are commonly prescribed anticonvulsants and p-hydroxyphenytoin is a major metabolite of phenytoin. Glutethimide is a sedative/hypnotic. Because of the similarity of their structures with those of barbiturates, even a small amount of any of these compounds may result in a false positive result for barbiturates, if the antibody (i.e., the polyclonal antibody in an antiserum) employed in an immunoassay for barbiturates is not sufficiently non-crossreactive with the interfering substances. Thus, an accurate and reliable immunoassay for barbiturates requires that antibody cross-reactivity with phenytoin, p-hydroxyphenytoin, glutethimide, and primidone be minimized. Unexpectedly, it has been found that the combination of the novel antiserum and tracers employed in FPIA's according to the present invention significantly improves the selectivity for barbiturates over phenytoin, p-hydroxyphenytoin, glutethimide, and primidone in that it maintains cross-reactivity for phenytoin and p-hydroxyphenytoin at about 0.5 and 1.0 %, respectively, and, for the other interferants, at below assay sensitivity.

The invention further provides test kits useful for determining barbiturates in an FPIA, including a single-step FPIA assay system such as the aforementioned Abbot Laboratories' TDx system. The kits comprise a novel tracer of the invention, or an aqueous solution or salt thereof, and novel antiserum of the invention, which recognizes both barbiturates and the tracer.

With regard to immunoassays of serum generally, wherein a transfer means (alternatively referred to as a dispensing means), such as a pipette or like device, is used to transfer a plurality of different serum samples into a tube or system, wherein the immunoassay is carried out, the invention provides an improvement. The improvement is to wash the transfer means between sample transfers with a solution of dimethylsulfoxide (within a narrow concentration range) and an alkali halide (similarly within a narrow concentration range) in water. Such washing has been found to be surprisingly effective in minimizing carryover of analyte being assayed for from one sample to another as a consequence of adhesion of the analyte to the dispensing means. Automated immunoassay systems, including FPIA systems such as Abbott Laboratories' TDx system, are examples of systems in which a dispensing means (e.g., a stainless steel or Teflon ®-coated stainless steel automated pipette) is used to transfer a plurality of samples into the system.

Kits in accordance with the invention for carrying out FPIAs for barbiturates can include such a wash solution, as well as buffers, diluents, antimicrobials such as sodium azide, stabilizers such as bovine serum albumin or bovine gamma globulin, substances such as copper sulfate to reduce background, and the like, as well known in the FPIA art.

Objects and advantages of the invention will be better understood from a reading of the following detailed description, including the examples.

DETAILED DESCRIPTION OF THE INVENTION

In one of its aspects, the invention entails a compound of Formula I

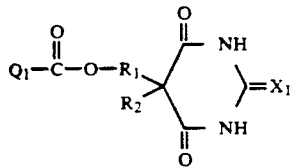

I wherein $X_1$ is oxygen or sulfur; $Q_1$ is (a) an activating group for nucleophilic displacement of $Q_1$ by an amino group, (b) an immunogenic polypeptide bonded to the carbonyl group through an N-terminal or side-chain amino group of the polypeptide, or (c) a moiety selected from the group consisting of fluorescein amine I, fluorescein amine II, and a fluorescein substituted at the 4'-position with a group of formula X $$-CH_2-(NH)R_{10}$$  X wherein $R_{10}$ is hydrogen, alkyl of 1-6 carbon atoms, or glycyl, said moiety bonded to the carbonyl group, to which $Q_1$ is bonded in the compound of Formula I, through the amino group of the moiety; $R_1$ is alkylene of 1 to 8 carbon atoms, cycloalkylene of 3 to 8 carbon atoms, alkenylene of 2 to 8 carbon atoms or cycloalkenylene of 5 to 8 carbon atoms; and $R_2$ is alkyl of 1 to 8 carbon atoms, cycloalkyl of 3 to 8 carbon atoms, alkenyl of 2 to 8 carbon atoms, cycloalkenyl of 5 to 8 carbon atoms, or phenyl provided that (i) $R_1$ is substituted at 0 or 1 carbon atom, other than the carbon bonded to the oxygen of the carbonate group, with chloro or bromo, (ii) $R_2$ is substituted at 0 or 1 carbon atoms with chloro or bromo, and (iii) if $R_2$ is phenyl, $R_1$ is other than ethylene.

Reference to a compound of the invention, i.e., a compound of formula I, is intended to encompass the various tautomeric and ionic forms, which the compound can have an aqueous solution at a pH between about 3 and about 9, and the various stereoisomers, which the compound can have, including those with both configurations at the asymmetric carbon at position 5 in the barbiturate ring.

Reference to "alkyl," "alkylene," "alkenyl" or "alkenylene" in the definitions of $R_1$ and $R_2$ in compounds of the invention includes both straight-chain and branched-chain alkyl, alkylene, alkenyl and alkenylene groups. Reference to "cycloalkyl," "cycloalkene," "cycloalkenyl" or "cycloalkenylene" in the definitions of $R_1$ and $R_2$ in compounds of the invention comprehends not only cyclic groups but also cyclic groups in which one or more of the carbon atoms can be substituted with an alkyl, alkylene, alkenyl or alkenylene group, provided that, in cycloalkyl and cycloalkylene groups, at least three carbon atoms are in the ring itself and, in cycloalkenyl and cycloalkenylene groups, at least five carbons are in the ring itself.

In another of its aspects, the invention entails a method of making an anti-barbiturate antiserum which comprises (a) immunizing a mammal with a compound of Formula II:

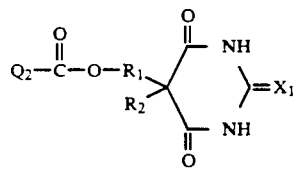

II wherein $R_1$, $R_2$ and $X_1$ are as defined for the compound of Formula I and $Q_2$ is a polypeptide that is immunogenic in the mammal and that is bonded to the carbonyl group through an N-terminal or side-chain amino group of the polypeptide; and (b) obtaining serum from the immunized mammal.

In still another aspect, the invention encompasses a process for assaying a biological sample for the presence of a barbiturate, said process comprising (a) combining in an aqueous solution, (i) the sample, (ii) an aliquot of an anti-barbiturate antiserum prepared by the process comprising (A) immunizing a mammal with a compound of Formula II:

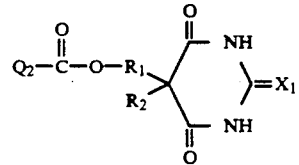

II wherein $R_1$, $R_2$ and $X_1$ are as defined for the compound of Formula I and $Q_2$ is a polypeptide that is immunogenic in the mammal and that is bonded to the carbonyl group through an N-terminal or side-chain amino group of the polypeptide; and (B) obtaining serum from the immunized mammal; and (iii) a compound of Formula I wherein $Q_1$ is a moiety selected from the group consisting of fluorescein amine I, fluorescein amine II, and a fluorescein substituted at the 4'-position with a group of formula X

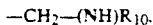
$$-CH_2-(NH)R_{10}. \qquad X$$

wherein $R_{10}$ is hydrogen, alkyl of 1-6 carbon atoms, or glycyl, said moiety bonded to the carbonyl group, to which $Q_1$ is bonded in the compound of Formula I, through the amino group of the moiety; said aqueous solution being at a pH at which the fluorescein moiety is fluorescent;

(b) passing plane polarized light through the solution resulting from step (a);

(c) measuring the polarization of fluorescence from the sample illuminated with plane polarized light in accordance with step (b); and (d) ascertaining whether any of one or more barbiturates is present in the sample by comparing the polarization of fluorescence measured in step (c) with the polarization of fluorescence determined, with an aliquot of the antiserum of the invention employed in step (a) and the fluorescent compound of the invention employed in step (a), for each of a plurality of calibrator samples, each comprising a known and different concentration of a barbiturate.

In still another aspect, the invention encompasses an improvement in a system for immunoassay of an analyte in mammalian serum, wherein transfer of a plurality of serum samples into the system is effected by repeated use of a transfer means. The improvement comprises washing the transfer means, between transfers of serum samples into the system, with a solution which consists essentially of 0.8 to 1.2 volumes of dimethylsulfoxide mixed with 1 volume of a solution which consists essentially of a salt, selected from the group consisting of NaCl, KCl, NaBr and KBr, at a concentration of 0.14 molar to 0.16 molar in water.

The invention further entails kits comprising reagents useful for determining barbiturates in a FPIA system, such as a system for carrying out the above-described FPIA method of the invention, including the TDx system commercially available from Abbott Laboratories, Inc. The kits comprise a tracer of the invention, i.e., a compound of Formula I wherein $Q_1$ is amino-derivatized fluorescein, or a salt thereof, and an antiserum of the invention, i.e., an antiserum made by the aforementioned process employing as immunogen a compound of Formula II, which recognizes both barbiturates and the tracer Kits in accordance with the invention for carrying out FPIAs for barbiturates can also include a wash solution in accordance with the invention, i.e., a solution which consists essentially of 0.8 to 1.2 volumes of dimethylsulfoxide mixed with 1 volume of a solution which consists essentially of a salt, selected from the group consisting of NaCl, KCl, NaBr and KBr, at a concentration of 0 14 molar to 0.16 molar in water, as well as buffers, diluents, antimicrobials, stabilizers, substances to reduce background, and the like as well known in the FPIA art.

A compound of Formula I, wherein $Q_1$ is an activating group for nucleophilic displacement from the carbonyl group, is an intermediate for synthesis of compounds of Formula I, wherein $Q_1$ is an immunogenic polypeptide or an amino derivative of fluorescein. As described below, a compound of Formula I, wherein $Q_1$ is an activating group for nucleophilic displacement, is preferably and facilely synthesized by methods, beginning with a dialkyl ester of malonic acid and proceeding through the analog of the compound wherein $-(C=O)Q_1$ is replaced with hydrogen, which do not involve using or making compounds which are controlled substances under the jurisdiction of the U.S. DEA.

The jurisdiction of the DEA extends to controlled substances per se as well as to substances, even if not controlled, that are made by using a controlled substance. Thus, because the compounds of Formula I, including those wherein Q. is an activating group for nucleophilic attack, are not controlled substances, the compounds of the invention advantageously avoid jurisdiction of the DEA, and the associated trouble and expense, when the preferred synthetic methods are employed to make the compounds of Formula I.

Numerous groups, which are activating groups for displacement from a carbonate carbonyl by nucleophilic attack by an amine nitrogen and which, consequently, are encompassed by $Q_1$ of Formula I, are known. These include chloro, bromo, fluoro, alkoxy (e.g., methoxy, ethoxy), substituted alkoxy (e.g., 2,2,2-trifluoroethoxy), alkenyloxy (e.g., isopropenyloxy), phenoxy, substituted phenoxy (e.g., p-nitrophenoxy, pentafluorophenoxy, 3,4-dichlorophenoxy), N-succinimidyloxy, N-phthalimidyloxy, imidazolyl, benzotriazolyloxy, or any of the other, similar leaving groups well known in the organic chemical art. Chloro is most preferred.

A compound of Formula I, wherein $Q_1$ is an immunogenic polypeptide, is an immunogen according to the invention. The immunogenic polypeptide in an immunogen according to the invention is any polypeptide or polyaminoacid which is suitable as a carrier protein to induce an immune response (i.e., production of antibodies) against a low molecular weight compound (i.e., an hapten), such as a barbiturate-derivative of Formula I wherein $Q_1$ is an activating group for nucleophilic attack, as defined above, when a conjugate of the hapten and the carrier protein is administered to a mammal in a manner, well known to those of skill in immunology, to induce an immune response in the mammal against the conjugate. Immunogenic polypeptides include both synthetic and naturally occurring polypeptides which have at least one free amino group that can form an amide linkage with the carbonate carboxyl of a barbiturate hapten in accordance with the invention (compound of Formula wherein $Q_1$ is an activating group for nucleophilic attack, as defined above). Immunogenic polypeptides include, among others, polylysines; hemocyanins, such as keyhole limpet hemocyanin; avian ovalbumins, such as chicken egg ovalbumin; mammalian immunoglobulins and gamma globulins; mammalian serum albumins, and mammalian thyroglobulins. The preferred immunogenic polypeptides (carrier proteins) for inclusion in a compound of Formula I (or Formula II) of the invention are bovine serum albumin (abbreviated "BSA") and bovine thyroglobulin (abbreviated "BThy"); most preferred is BSA. Many commonly used carrier proteins, including BSA and BThy, can be purchased in a form suitable for use as a carrier protein in accordance with the invention (typically at least about 95 % pure) from any of a number of sources, such as Sigma Chemical Company, St. Louis, Mo., U.S.A. It will be understood that, in a molecule of an immunogen of Formula II according to the invention, it is possible for more than one molecule of hapten to be conjugated to each molecule of carrier protein; in fact, it is preferred that, on the average, at least ten molecules of hapten be conjugated to each molecule of carrier protein.

A compound of Formula I, wherein $Q_1$ is an amino derivative of fluorescein, is a tracer in accordance with the invention.

As explained above, and well understood in the immunoassay arts, and particularly the FPIA art, the tracers of the invention are analyte analogs of barbiturates. As such, the analog analytes compete, with any barbiturate present in a sample being assayed in an FPIA according to the invention, for binding to barbiturate-recognizing antibody in an antiserum according to the invention. The tracer in an assay system, both bound (to such antibody) and free, is detectable because of the fluorescence emitted by the fluoresceinyl moiety; but, as explained above, the polarization of the fluorescence from antibody-bound tracer is significantly higher than that from free tracer (which is essentially completely depolarized), so that measurement (by any of numerous well known methods) of polarization of fluorescence from the fluoresceinyl moiety in a sample is a measure of the concentration of bound tracer which, in turn, is inversely proportional to the concentration of barbiturates that, like the tracer, are recognized by the antibody in the antiserum.

The fluoresceinyl moiety in a tracer according to the invention can, like fluorescein itself, as indicated in FIG. IV, below, be in the acid (or "open") tautomeric form or the lactone (or "closed") tautomeric form, with the ratio of the concentrations of the two forms depending on the pH of the solution. FIG. IV also illustrates the numbering of the fluoresceinyl moiety employed in this specification.

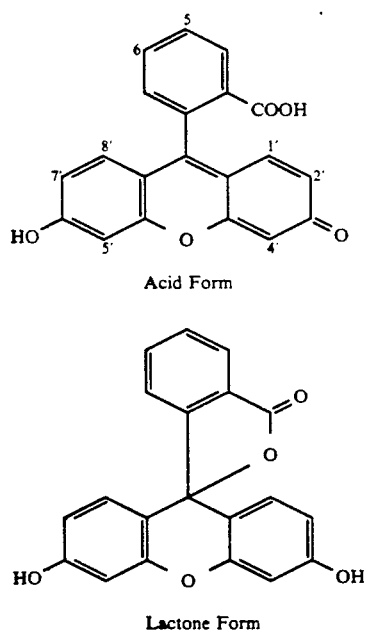

Figure IV

Acid Form

Lactone Form

The acid form is fluorescent, absorbing light with a wavelength in the blue part of the visible range and, after a fluorescence decay half-life of about 4 nanoseconds, emitting light in the green part of the visible range. In an assay according to the invention, the pH of the solution is set so that, preferably, the acid form of the fluoresceinyl moiety of the tracer predominates in concentration significantly over that of the lactone form. Thus, a pH in such a solution of between about 3 and about 12 is workable, but between about 5 and about 10 is preferable and between about 6 and about 8 is most preferable.

Amino-derivatives of fluorescein are employed to make the tracers of the invention, by formation of an amide between the amino (primary or secondary) of the fluorescein derivative and the carbonyl of the carboxylate bonded to the $R_1$ group of the tracer. Thus, $Q_1$ in a tracer according to the invention can be, among others, fluorescein amine I (5-aminofluorescein), fluorescein amine II (6-aminofluorescein), or a fluorescein substituted at the 4'-position with a group of formula X $$-CH_2-(NH)R_{10}. \quad\quad X$$

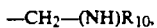

wherein $R_{10}$ is hydrogen, alkyl of 1-6 carbon atoms, or glycyl ($-(C=O)CH_2NH_2$). Most preferred are tracers wherein Q1 is 4'-aminomethylfluorescein (abbreviated "AMF").

Synthesis of the precursors of the intermediates of the invention, i.e., derivatives of compounds of Formula I wherein $Q_1-(C=O)-$ is replaced with hydrogen, is taught in detail in the examples that follow, beginning with the dialkyl ester of malonic acid, diethyl malonate, as the starting material. (Dimethyl malonate could be employed equally as well.) Generally, the dialkyl malonate is first alkylated with a reagent which contains a protected hydroxyl, which is unmasked later. Treatment with urea produces a 5-monosubstituted barbituric acid, which is then alkylated a second time to introduce another group in the 5-position. The treatment with urea could be carried out after the second alkylation. The protected hydroxyl is then unmasked to allow synthesis of the corresponding intermediate of the invention (i.e., compound of Formula I wherein $Q_1$ is an activating group for nucleophilic displacement). The examples teach a number of variations on this general approach. For example, the skilled will recognized that the order of the alkylations can be reversed, such that the group containing the protected hydroxyl is introduced second rather than first. The precursors wherein $X_1$ is sulfur are made in the same ways as those wherein $X_1$ is oxygen, except that, in the formation of the barbiturate ring, thiourea is employed in place of urea. (Oxygen is preferred for $X_1$.)

The intermediates of the invention, i.e., compounds of Formula I wherein $Q_1$ is an activating group for nucleophilic displacement of itself from the carbonyl of the carbonate by a (primary or secondary) amino group, are made by well known methods by reacting, in a suitable solvent such as benzene, acetonitrile, tetrahydrofuran or dimethoxyethane, the hydroxylic precursor with an activating reagent that forms a reactive ester at the hydroxyl group. Among these activating reagents are phosgene, carbonyl dibromide, carbonyl difluoride, 2,2,2-trifluoroethyl chloroformate, trichloromethyl chloroformate, phenylcarbonate, substituted phenyl carbonate, methylcarbonate, ethylcarbonate, carbonyl diimidazole, carbonyl dibenzotriazole, and, as well understood by the skilled in organic chemistry, like compounds corresponding to the many activating groups that can be bonded to the carbonate in the compound of Formula I (see above for examples). Most preferably, the hydroxylic precursor is reacted with phosgene in benzene to provide the intermediate of Formula I, wherein $Q_1$ is chloro.

An immunogen of the invention (i.e., a compound of Formula II) is made from an intermediate of the invention by simply combining the immunogenic polypeptide and the intermediate (in a large molar excess relative to the polypeptide) in an aqueous solution buffered to a pH of between about 7 and 9, allowing the conjugation reaction to proceed in the solution for between about 1 hour and about 5 hours at ambient (i.e., room temperature (about 23 deg. C) and nearly 1 atmosphere pressure), and then separating the resulting conjugate (and any unreacted polypeptide) from intermediate and other low molecular weight compounds by exhaustive dialysis against an aqueous buffer or by size exclusion chromatography. In this regard, see Examples 9 and 12 below.

The tracers according to the invention, i.e., the compounds of Formula I wherein $Q_1$ is an amino-derivative of fluorescein, are made by simply combining the fluorescein derivative and the intermediate of the invention corresponding to the compound of Formula I in approximately equimolar amounts in a suitable solvent, such as dimethylformamide, in the presence of a large molar excess (e.g., two equivalents) of a base, such as triethylamine or another, preferably volatile trialkylamine, allowing the nucleophilic displacement between the fluorescein derivative and the intermediate to occur for about 6 to about 24 hours at ambient conditions, and then, preferably after removal of solvent in vacuo at ambient temperature, chromatographically purifying the tracer. In this regard, see Example 1 below.

The immunogens according to the invention are used to make anti-barbiturate antibody for use in FPIA's according to the invention. The antibody made with the immunogens is polyclonal. The antibody can be made by in vitro immunization with an immunigen of the invention of mammalian cells (e.g., lymphocytes or splenocytes) in culture that are capable of producing antibody, employing methods known in the immunological arts for production of polyclonal antibody by such in vitro immunization methods. More preferably, however, the polyclonal antibody is provided as part of an anti-barbiturate antiserum of the invention.

An antiserum of the invention is made by a standard method employing an immunogen of the invention to immunize a mammal and then obtaining serum from the mammal after it has raised an immune response against the immunogen. Mammals that can be employed to provide antisera according to the invention include, among others, sheep, goats, rabbits, mice and rats. Sheep are preferred. Further, it is preferred that the immunogenic polypeptide of the immunogen of the invention used to make an antiserum of the invention be a polypeptide that is foreign to the species of mammal employed to make the antiserum. Bovine serum albumin is the most preferred immunogenic polypeptide in immunogens of the invention. The details of preparing an antiserum according to the invention will, as the skilled in immunology will understand, vary somewhat, depending on the species, age, weight and other characteristics of the mammal employed, the titer of anti-barbiturate antibody sought, the composition of the inocula used (e.g., whether adjuvant is employed and, if so, which adjuvant and at what concentration; concentration of immunogen), and other factors. Nonetheless, it is well within the skill of the person of ordinary skill to readily prepare an antiserum of the invention using any species of mammal. Typically, in preparing an antiserum of the invention, an immunogen will be administered, in combination with an adjuvant, such as Freund's complete or incomplete in a physiologically acceptable, aqueous solution, such as physiological saline, to a mammal by subcutaneous or intravenous injection several times over about two weeks to about three months. After some further period of time after the last injection, from about a week to about three months, blood will be taken periodically from the inoculated mammal, serum prepared from the blood by a standard technique (involving basically removing the cells from the blood), and the serum analyzed for titer of anti-barbiturate antibody. Once a titer of antibody that is deemed to be acceptable is reached, a large amount of blood will typically be taken from the animal and the serum obtained from this blood will be stored and used as needed in assays or for preparing test kits for assays. A mammal producing anti-barbiturate antibody at an acceptable titer in its serum as a result of immunization with an immunogen of the invention will typically be maintained for as long as possible in an attempt to have a source of antiserum that is as nearly uniform as possible in its relevant properties. Other than being mixed with buffers, stabilizers, and antimicrobials, substances that reduce background and the like, as described, for example, in Example 13 below, an antiserum of the invention is used as obtained after removal of cells from blood taken from the mammal providing the antiserum.

In many immunoassay systems, FPIA and other, particularly automated systems, a single transfer means is used repeatedly to transfer different samples into the system for analysis. This presents a problem of "carryover," as analyte that is present in one sample may adhere to the transfer means and be carried into samples that are transferred later, potentially yielding falsely positive or falsely high concentrations of analyte in the later transferred samples. To minimize this problem of carryover, the repeatedly used transfer means must be washed with a wash solution between transfers. In the course of making the present invention, we have found a wash solution that is surprisingly effective in minimizing carryover in immunoassays of serum samples. This solution has as its essential components (i.e., consists essentially of) water, dimethylsulfoxide and an alkali halide selected from the group consisting of NaCl, KCl, NaBr and KBr, NaCl being preferred. (By reference herein to "consisting essentially of" is intended that components, other than those stated, are not present in the composition in significant amounts, although minor and insignificant amounts of other components (e.g., dissolved air, minor and insignificant amounts of other components, including other salts or other types of substances present as impurities) may be present. A wash solution of the invention is made by combining, into a solution, usually at ambient conditions, between 0.8 and 1.2 volumes of dimethylsulfoxide with 1 volume of a solution that consists essentially of between 0.14 molar and 0.16 molar (preferably about 0.15 molar) NaCl, KCl, NaBr or KBr in water. Any transfer means used to transfer samples of serum into a tube, microtiter plate well, millititer plate well or other sample holder in which an immunoassay, or a part thereof, is carried out can be washed advantageously with a wash solution of the invention. Typically the transfer means (or "dispensing means," as it may sometimes be called) is some type of tube, such as a pipette, used to deliver a predetermined volume of a fluid (e.g., serum sample) from one vessel to another, as well understood in the art. Among transfer means which are pipettes, with which the wash solution can be used advantageously, are manually operated pipettes, Eppendorfs, and automated pipettes, which can be made of glass, plastic (including neoprene, Teflon ® or the like), stainless steel, plastic-coated stainless steel, Teflon-coated stainless steel or the like. The wash solution of the invention is used by simply rinsing the transfer means thoroughly at least, and preferably, one time between transfers of sample, with each rinse being with a fresh aliquot of wash solution and with each aliquot of wash solution, after use in a rinse of a transfer means, being discarded.

A kit according to the invention for carrying out FPIA's of serum samples for barbiturates, such as using the Abbott Laboratories' TDx system, can advantageously include a wash solution of the invention, in a vial or other type of container separate from the vial(s), container(s) or the like which hold antiserum of the invention and tracer of the invention.

The antisera and tracers of the invention are employed in FPIA's according to the invention for barbiturates in biological samples, preferably samples of human urine or serum, most preferably samples of human serum.

The FPIA barbiturate assay, in accordance with the present invention, involves mixing the anti-barbiturate antiserum of the invention and barbiturate-analog tracer with a sample being assayed for the presence of one or more barbiturates. The concentration of antibody specific for barbiturates and barbiturate-analog (fluorescent) tracer is very much lower than that of the tracer and likely also those of the barbiturates (if present in the sample). The barbiturates (if any) and the tracer compete for limited antibody binding sites, resulting in the formation of antibody-fluorescent analyte analog complexes and, if barbiturate analyte is present, also antibody-analyte complexes. By maintaining a constant concentration of tracer and antibody (from samples of the same antiserum) for a set of assays of different samples, including calibration samples ("calibrators") of known barbiturate concentration, the ratio of barbiturate-antibody complex to tracer-antibody complex formed upon incubation is directly proportional to the amount of barbiturates in the samples and inversely proportional to the net polariation of fluorescence observed with the samples. Therefore, by comparison of fluorescence polarization from a test sample (i.e., a sample being tested for the presence of a barbiturate) with fluorescence polarization as a function of barbiturate concentration in calibrator samples, with all polarization measurements made in systems which have the same tracer, same concentration of tracer, same antiserum and same concentration of anti-barbiturate antibody in the antiserum, one is able to at least qualitatively determine the amount of barbiturates contained in the sample.

An FPIA according to the invention can be any type of FPIA, manual or automated. It is preferred, however, that an FPIA according to the invention be carried out in a one-step, automated system, such as the TDx system, which is available commercially from Abbott Laboratories, Inc. (Irving, Tex., U.S.A.).

Any combination of antiserum according to the invention and tracer according to the invention can be employed in an FPIA according to the invention. It is acceptable, but not preferable, to employ in combination antisera prepared with more than one immunogen of the invention or, in combination, more than one tracer of the invention in an FPIA of the invention. It is preferred that antiserum prepared with a single immunogen of the invention and a single tracer of the invention be employed in an FPIA according to the invention and that, in such an FPIA, the group $R_1$ in the tracer differs from the group $R_1$ in the immunogen used to make the antiserum and the group $R_2$ in the tracer differs from the group $R_2$ in the immunogen used to make the antiserum. These differences in the $R_1$ and $R_2$ groups advantageously facilitate competition, for binding with antibody of the antiserum, of barbiturate analyte vis a vis tracer in the FPIA procedure. The most preferred combination of antiserum and tracer for an FPIA of the invention is sheep antiserum prepared with the immunogen of FIG. 21 (see Example 9) and tracer of FIG. 1 (see Example 1).

The skilled will understand that there are many and wide variations in the detailed conditions that can be employed successfully in carrying out an FPIA, including an FPIA according to the invention for barbiturates, including in human urine or serum. One detailed protocol for carrying out an FPIA according to the invention is provided in the examples. This protocol is not intended to be limiting but, rather, is intended to be illustrative of a working FPIA system and a guide in establishing protocols to carry out FPIA's according to the invention.

The surprisingly and advantageously broad range of barbiturates that can be sensitively detected in an FPIA of the invention, and the surprising and advantageous insensitivity of an FPIA of the invention for common interferants in assays for barbiturates, are illustrated in Examples 14 and 15 below. As can be seen from those examples, the analytes detectable in accordance with the present invention include the barbiturates amobarbital, aprobarbital, brallobarbiral, butabarbital, butalbital, pentobarbital, phenobarbital, secobarbital, and talbutal, among others.

Indeed, prior to the present invention, a practicable system for assay of a broad range of barbiturates in human serum was not available.

Carrying out an FPIA of the invention is facilitated with a test kit according to the invention, as described hererofore. In a kit according to the invention, antiserum according to the invention (typically diluted in an appropriate buffer adjusted to an appropriate pH and containing stabilizers, such as ethylene glycol and bovine serum albumin, antimicrobials such as sodium azide, and the like, see Example 13) will be held in one container, tracer according to the invention (typically dissolved in an aqueous buffer, which may also contain stabilizers and the like, see Example 13) will be held in a separate container, and other solutions that may be included in the kit, including a wash solution according to the invention, a "pretreatment" solution, and calibrator and a diluent buffer, or the like, will be held in still further containers (again, refer to Example 13). Any type of container, of which a large number are well known to the skilled and which are suitable for holding and transporting such solutions, can be employed, including, for example, glass or plastic vials with, preferably, screw top covers.

Representative buffers that can be employed in the solutions employed in carrying out an FPIA according to the invention include, among others, borate, phosphate, carbonate, tris, and the like. The particular buffer employed is not critical to the present invention, but phosphate buffer is preferred.

The preferred procedure descried below in Example 13 for an FPIA according to the invention can be employed advantageously with not only the ABBOTT LABORATORIES' TDx Clinical Analyzer but also the ABBOTT LABORATORIES' automated abused drug systems, such as the ADx® or IMx®, all of which are commercially available from Abbott Laboratories, Irving, Tex. It is to be understood that when these systems are used, the assay is fully automated from beginning to final reading. However, a manual assay can be performed. In the case of automated and manual assays, half of the sample is mixed with half of the pretreatment solution and half of the dilution buffer and a background reading is taken. Then the other half of the sample is combined, together with diluted antiserum and tracer solution, with the other half of the pretreatment solution and the other half of the dilution buffer. See the final two sentences of step 1 and step 2 of the protocol described in Example 13. Then, after incubation, a fluorescence polarization reading is taken and processed to yield information on whether barbiturates are present in the test solution.

The following examples describe and illustrate the present invention further. In the examples, a capital C standing alone represents "degrees Celsius".

EXAMPLE 1

In this Example, the synthesis of the most preferred tracer of the invention, 5-{3-[(4'-fluoresceinyl)methylaminocarbonyloxy]cyclopent-1-yl}-5-propylbarbituric acid, illustrated in FIG. 1, is described.

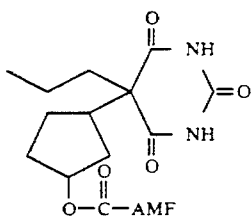

Figure 1

Cyclopentenediol

To a mechanically-stirred suspension of 76 g (0.34 mole) 35% peracetic acid (previously treated with 2 g sodium acetate) and 91.4 g (0.86 mole) powdered sodium carbonate in 500 mL anhydrous dichloromethane was added dropwise 45.548 g (0.69 mole) of freshly depolymerized cyclopentadiene over 45 min, with periodic cooling in an ice bath. After stirring for 1 hr, the reaction was filtered, and the filter cake washed with 200 mL dichloromethane. The combined filtrate and washes were added over 1 hr to 250 mL of water cooled to 0-5 C. The mixture was stirred an additional 10 hr. The dichloromethane layer was separated and extracted 2×50 mL with water. The water was removed on a rotary evaporator, and the residue distilled at 0.3 mm Hg to provide 14.169 g clear colorless oil, bp 82-85 C.

4-(t-Butyldimethylsilyloxy)-cyclopent-2-ene-1-ol

To 1.592 g (15.9 mmol) of the oil, prepared as described in the preceding paragraph, was added successively 20 mL dimethylformamide, 1.51 g (22.3 mmol) imidazole, and 2.39 g (15.9 mmol) t-butyldimethylsilyl chloride. The resulting solution was stirred for 12 hrs, diluted with 100 mL of diethyl ether, and extracted 6 × (i.e., six times), each with 2 mL water. The organic phase was dried over MgSO$_4$, filtered, and concentrated. Chromatography on a 2×18 cm column, packed with hexane and eluted with 100 mL each of 2%, 4%, 6%, 10%, 15%, and 20% ethyl acetate/hexane provided 683 mg clear colorless oil in 12 mL fractions 26-35.

4-(t-Butyldimethylsilyloxy)-1-iodocyclopent-2-ene

A solution of 1.25 g (4.79 mmol) triphenylphosphine in 4.5 mL diethyl ether was added to a solution of 325 mg (4.79 mmol) imidazole in 1.5 mL acetonitrile, and the resulting mixture was cooled to 0 C and treated successively with 1.13 g (4.47 mmol) iodine (in portions) followed by the oil prepared as described in the immediately preceding paragraph. After stirring for 1 hr at ambient, the reaction mixture was concentrated to an oily sludge. This sludge was dissolved in a minimum amount of dichloromethane, and filtered through a 2×10 cm column of silica gel, packed with 20% diethyl ether/hexane, using 80 mL 20% diethyl ether/hexane to elute. Concentration provided 1.427 g of a yellow-orange oil, which was used immediately in the following reaction.

Diethyl 1-[4-(t-Butyldimethylsilyloxy)cyclopent-2-enyl]malonate

The iodide of the immediately preceding paragraph was added as a solution in 2 mL tetrahydrofuran to a solution of 105 mg (3.51 mmol, 80% oil dispersion) sodium hydride, previously washed 3 times, each with 5 mL pentane, and 0.53 mL (3.51 mmol) diethyl malonate in 2 mL dimethylformamide, previously stirred for 1 hr at ambient. The orange color rapidly dissipated; and, after 30 min, the reaction mixture was refluxed for 12 hr. The mixture was then cooled, acidified with 1N HCl to pH 3, and extracted 3 times, each with 15 mL ethyl acetate. The extracts were dried over MgSO$_4$, filtered, and concentrated. Chromatography on a 2×18 cm silica gel column packed with hexane, and eluted with 50 mL each of 2%, 4%, 6%, 8%, and 100 mL 10% ethyl acetate/hexane provided 697 mg clear colorless oil in 12 mL fractions 13-17.

Diethyl 1-[4-(t-Butyldimethylsilyloxy)cyclopen-2-enyl]allylmalonate

The oil prepared immediately above was dissolved in 1.5 mL dimethylformamide, and the solution added to a suspension of 32 mg (1.08 mmol, 80% oil dispersion) sodium hydride, previously washed 3 ×, each with 5 ml pentane, in 0.5 mL dimethylformamide and 0.5 mL tetrahydrofuran. After stirring for 1 hr, a clear light brown solution developed, and 110 μL (1.27 mmol) allyl bromide was added. The solution was stirred at ambient for 12 hrs. The reaction was diluted in ethyl acetate and quenched with 0.5 mL water. The organic phase was dried over MgSO$_4$, filtered, and concentrated. Chromatography on a 1×18 cm silica gel column, packed with hexane and eluted with 50 mL 4% and 50 mL 8% ethyl acetate/hexane, provided 169 mg of a clear colorless oil in 6 mL fraction 5, and an additional 184 mg in fractions 6-9.

Diethyl 1-[4-(t-Butyldimethylsilyloxy)cyclopentyl]propylmalonate

The 169 mg (0.43 mmol) dialkenylated malonate in fraction 5 from the chromatographic procedure described at the end of the immediately preceding paragraph was dissolved in 10 mL absolute ethanol and combined with 17 mg 10% palladium on carbon. The mixture was flushed with hydrogen and hydrogenated at 47-51 psi for 2 hrs. The catalyst was removed by filtration, and the filtrate concentrated to provide 158 mg of a clear colorless oil.

5-{1-[4-(t-Butyldimethylsilyloxy)cyclopentyl]}-5-propylbarbituric acid

To a solution of 35 mg (1.50 mmol) sodium and 35 mg (0.57 mmol) urea in 3 mL absolute ethanol was added the oil obtained in the procedure described in the immediately preceding example. The ethanol was removed by distillation, and the residual syrup heated to 80 C for six hrs., allowed to cool, and then stirred for 12 additional hrs. The syrup was then diluted in ethyl acetate and acidified to pH 4 with 1N HCl. The organic phase was separated, dried over MgSO$_4$, filtered, and concentrated. Chromatography on a 1×12 cm silica gel column, packed with chloroform and eluted with 50 mL 3% methanol/chloroform and 50 mL 6% methanol/chloroform, provided 28 mg of a clear colorless oil in 7 mL fraction 3, and an additional 68 mg in fractions 4-7.

5-[1-(4-Hydroxycyclopentyl]-5-propylbarbituric acid

The 28 mg obtained in fraction 3 in the procedure of the paragraph immediately above was dissolved in 0.5 mL acetonitrile. The solution was cooled to 0 C and treated with 1 drop 48% aqueous hydrofluoric acid. After stirring for 35 mins, the reaction mixture was concentrated, the residue was dissolved in methanol, and the resulting solution was streaked onto a 0.25 mm×20 cm×20 cm silica gel plate and eluted with 6% methanol/chloroform. Elution of the major band with 80% methanol/chloroform and concentration provided 12.5 mg of a white solid. Rechromatography on an additional plate as just described provided 2 mg and 10 mg white solids as separate bands.

5-{3-[(4'-Fluoresceinyl)methylaminocarbonyloxy]-cyclopent-1-yl}-5-propylbarbituric acid To a solution of a 2.5 mg (9.8 μmol) portion of the major (10 mg) product described immediately above in 0.2 mL tetrahydrofuran was added 0.3 mL of a 12% solution of phosgene in benzene. After stirring for 1 hr., the solution was concentrated in a stream of dry nitrogen, redissolved in 50 μL dimethylformamide, and treated with a solution of 3.9 mg (9.8 μmol) aminomethylfluorescein hydrochloride (i.e., 4'-[aminomethyl]-fluorescein hydrochloride) and 2.8 μL (19.6 umol) triethylamine in 50 μL dimethylformamide. After stirring the reaction mixture for 12 hrs. at ambient, the solvents were pumped off and the residue was redissolved in methanol and streaked onto a 0.25 mm×20 cm×20 cm silica gel plate. Development with 10% methanol/chloroform, elution of the major band with 80% methanol/chloroform, and concentration provided 5.1 mg of the tracer as an orange solid. Further purification of the tracer could be achieved by reversed phase chromatography on a C18 plate, eluting with 50% acetonitrile/water.

EXAMPLE 2

5-{1-[(4'-Fluoresceinyl)methylaminocarbonyloxy]pent-4-yl}-5-allyl barbituric acid The title tracer of this example is illustrated in FIG. 3:

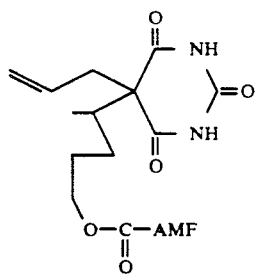

Figure 3

4-Bromo-1-pentanol

To a solution of 1.00 g (4.78 mmol) of ethyl 4-bromopentanoate in 10 mL tetrahydrofuran was added 167 mg (7.66 mmol) lithium borohydride. After stirring 12 hrs at ambient, the mixture was diluted in diethyl ether, cooled to 0 C, and quenched with equal portions of water and saturated NH$_4$Cl until no more hydrogen was evolved. The organic phase was dried over MgSO$_4$, filtered, and concentrated to 1.063 g of a colorless, slightly cloudy viscous oil.

1-(2-Ethoxy)ethoxy-4-bromopentane

The cloudy oil prepared above was dissolved in 2 mL ethyl vinyl ether and cooled to 0 C. Several crystals of p-toluenesulfonic acid monohydrate were added, and the reaction was warmed to ambient and stirred for 1 hr. The reaction mixture was concentrated and then chromatographed directly on a 2×18 cm silica gel column, packed with hexane, and eluted with 100 mL 5% and 100 mL 10% diethyl ether/hexane. Concentration of 10 mL fractions 7-17 provided 872 mg of a clear colorless oil.

Diethyl [1-(2-ethoxy)ethoxypent-4-yl]malonate

Sodium (83 mg, 3.63 mmol) was dissolved in 1.5 mL absolute ethanol. Diethyl malonate (0.55 mL, 3.63 mmol) was then added, followed by the oil prepared as described in the paragraph immediately above and 180 mg (1.21 mmol) sodium iodide. The mixture was refluxed for 12 hrs, cooled, quenched with water, and extracted 3 ×, each with 20 mL ethyl acetate. The extracts were dried over MgSO$_4$, filtered, and concentrated. Chromatography on a 2×18 cm silica gel column, eluting with 100 mL 5%, 100 mL 10%, and 100 mL 50% ethyl acetate/hexane, provided 861 mg of a clear, colorless oil in 12 mL fractions 21-24.

Diethyl [1-(2-ethoxy)ethoxypent-4-yl]allylmalonate 341 mg (2.98 mmol) potassium hydride (35% mineral oil suspension) was washed 3 ×, each with 5 mL hexane, and suspended in 2.0 mL dimethylformamide. A solution of the malonate made as described in the immediately preceding paragraph, in 1.0 mL tetrahydrofuran, was added, and the mixture stirred for 1 hr to yield a light brown solution. Allyl bromide (0.28 mL, 3.25 mmol) was then added, and the mixture was stirred for 1 hr at ambient and then refluxed for 3 hr. The mixture was cooled, quenched with water, and extracted 4 ×, each with 15 mL ethyl acetate. The organic phases were dried over MgSO$_4$, filtered, and concentrated to give an oil. The oil was chromatographed on a 2×18 cm silica gel column, packed with hexane and eluted with 100 mL 5%, 100 mL 8%, and 100 ml 10% ethyl acetate/hexane. Concentration of 12 mL fractions 8–14 provided 614 mg clear colorless oil.

5-[1-(2-ethoxy)ethoxypent-4-yl]-5-allylbarbituric acid

Sodium (133 mg, 5.76 mmol) was dissolved in 2 mL absolute ethanol, and 131 mg (1.92 mmol) urea was added. A solution of 599 mg of the malonate, made as described in the immediately preceding paragraph, in 0.5 mL ethanol was added, and the solution was refluxed for 12 hr. Most of the ethanol was removed by rotary evaporation, and the reaction was quenched with water and extracted 4 ×, each with 10 mL of ethyl acetate. The combined extracts were dried over MgSO$_4$, filtered, and concentrated. Chromatography on a 1×18 cm column, packed with chloroform and eluted with 30 mL chloroform, 50 mL 3%, and 50 mL 6% methanol/chloroform furnished 299 mg via concentration of 6 mL fractions 6–12.

5-(1-Hydroxypent-4-yl)-5-allyl barbituric acid 104 mg (0.32 mmol) of the product prepared as described in the immediately preceding paragraph was dissolved in 3 mL ethanol and treated with 0.2 mL 5% sulfuric acid at reflux for 10 mins., at which point TLC showed no starting material. The solution was filtered through a 1×12 cm silica gel column, packed and eluted with 10% methanol/chloroform, and the eluent concentrated to 61 mg of a white solid. The solid was dissolved in methanol, and streaked onto a 0.5 mm×20 cm×20 cm plate. Development with 10% methanol/chloroform, and elution of the major band with 80% methanol/chloroform, produced 39 mg of a white solid.

5-{1-[(4'-Fluorescenyl)methylaminocarbonyloxy]pent-4-yl}-5-allyl barbituric acid 3.0 mg (9.4 μmol) of the white solid, made as described in the immediately preceding paragraph, was converted into the title tracer by the same method, described in the final paragraph of Example 1, used to prepare the tracer of Example 1.

EXAMPLE 3

5-{1-[4-(4'-Fluoresceinyl)methylaminocarbonyloxy]-pent-4-yl}-5-propylbarbituric acid The title tracer of this example is illustrated in FIG. 2:

Figure 2

Diethyl [1-(2-ethoxy)ethoxypent-4-yl]propylmalonate 57 mg (0.17 mmol) of diethyl 2-[1-(2-ethoxy)ethoxypent-4-yl]-2-allylmalonate prepared above was dissolved in 10 mL absolute ethanol and combined with 6 mg (56 umol) 10% palladium on carbon. The mixture was flushed with hydrogen and hydrogenated for 4 hrs at 44 psi. Removal of the catalyst by filtration through Celite ® brand diatomite and concentration provided 53 mg of a colorless oil.

5-[4-(1-Hydroxypentyl)]-5-propylbarbituric acid 81 mg (0.25 mmol) of the compound from the immediately preceding paragraph was dissolved in 2 mL tetrahydrofuran and reacted with 4 drops of a 1N HCl solution for 2 hrs. The reaction mixture was concentrated and streaked onto 2 0.5 mm×20 cm×10 cm (high) plates. Development with 15% methanol/chloroform and elution of the major band with 50% methanol/chloroform provided 40 mg of a white semisolid.

5-{1-[4-(4'-Fluoresceinyl)methylaminocarbonyloxy]-pent-4-yl}-5-propylbarbituric acid This aminomethylfluorescein tracer was prepared as described in the final paragraph of Example 1 from 3 mg of 5-[4-(1-hydroxypentyl)]-5-propylbarbituric acid.

EXAMPLE 4

5-{4-[(4'-Fluoresceinyl)methylaminocarbonyloxy]cyclohex-1-yl}-5-allylbarbituric acid The title tracer of this example is illustrated in FIG. 5:

Figure 5

4-(t-Butyldimethylsilyloxy)cyclohexan-1-ol

One gram of 1,4-cyclohexanediol was silylated as described in the preparation of 4-(t-butyldimethylsilyloxy)-cyclopent-2-ene-1-ol in Example 1 above.

4-(t-Butyldimethylsilyloxy)-1-iodocyclohexane

This iodide was prepared as described for the preparation of 4-(t-butyldimethylsilyloxy)-1-iodocyclopent-2-ene in Example 1 above.

Diethyl 1-[4-(t-Butyldimethylsilyloxy)cyclohexyl]malonate

The title compound was prepared as described for the preparation of diethyl 1-[4-(t-butyldimethylsilyloxy)cyclopent-2-enyl]malonate in Example 1 above.

Diethyl 1-[4-(t-Butyldimethylsilyloxy)cyclohexyl]allylmalonate

This dialkylated malonate was prepared exactly as described for the preparation of diethyl 1-[4-(t-butyldimethylsilyloxy)cyclopent-2-enyl]allylmalonate of Example 1 above.

5-{1-[4-(t-Butyldimethylsilyloxy)cyclohexyl]}-5-allylbarbituric acid

The barbituric acid derivative was prepared exactly as described for 5-{1-[4-(t-butyldimethylsilyloxy)cyclopentyl]}-5-propylbarbituric acid of Example 1 above.

5-{1-[4-Hydroxycyclohexyl]}-5-allylbarbituric acid

The ether was deprotected as described for the preparation of 5-[1-(4-hydroxycyclopentyl]-5-propylbarbituric acid in Example 1 above.

5-{4-[(4'-Fluoresceinyl)methylaminocarbonyloxy]cyclohex-1-yl}-5-allylbarbituric acid This tracer was prepared from the 4'-hydroxycyclohexyl analog exactly as described in the final paragraph of Example 1 for 5-{3-[(4'-fluoresceinyl)methylaminocarbonyloxy]cyclopent-1-yl}-5-propylbarbituric acid, the tracer of Example 1.

EXAMPLE 5

5-{3E-4-[(4'-Fluoresceinyl)methylaminocarbonyloxy]-3-methyl-2-butenyl}-5-allylbarbituric acid The title tracer of this example is illustrated in FIG. 6:

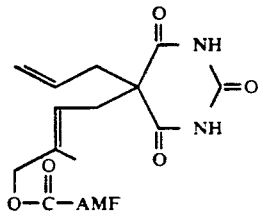

Figure 6

Diethyl 3,3-dimethylallylmalonate 422 mg (14.1 mmol, 80% mineral oil dispersion) sodium hydride was washed 3 ×, each with 5 mL pentane, and suspended in a mixture of 10 mL tetrahydrofuran and 5 mL dimethylformamide. 2.04 g (13.4 mmol) diethyl malonate was added, and the mixture stirred for 40 mins to form a clear light brown solution. Prenyl bromide (2.00 g, 13.4 mmol) was then added, and the solution refluxed for 1 hr. The reaction was quenched with water, acidified to pH 2 with 1N HCl, and extracted 2 ×, each with 10 mL diethyl ether. The organic phases were dried over MgSO$_4$, filtered, and concentrated. Chromatography on a 2×18 cm column, packed with hexane and eluted with 50 mL each of 2%, 4%, 7%, 10%, and 15% diethyl ether/hexane, furnished 2.734 g of a clear colorless oil in 12 mL fractions 4–16.

(3,3-Dimethylallyl)barbituric acid

To a solution of 70 mg (3.03 mmol) of sodium in 1 mL absolute ethanol was added 61 mg (1.01 mmol) urea followed by a solution of 200 mg (0.88 mmol) of the malonate prepared as described in the paragraph immediately above in 1 mL of absolute ethanol. One mL of ethanol was removed by distillation, and the remaining solution refluxed overnight. The solution was acidified to pH 3 with 1N HCl and extracted 2 ×, each with 10 mL of ethyl acetate. The combined organic phases were dried over MgSO$_4$, filtered, and concentrated to 214 mg of a white solid.

5-(3,3-Dimethylallyl)-5-allylbarbituric acid

To a solution of the above solid in 0.5 mL tetrahydrofuran and 1.0 mL dimethylformamide was added 33 mg (1.09 mmol) sodium hydride (80% mineral oil dispersion). The solution was stirred for 1 hr, 0.11 mL of allyl bromide was added, and the resulting solution stirred for 48 hrs. The reaction was quenched with 1N HCl to pH 3 and extracted 3 ×, each with 10 mL of ethyl acetate. The organic phases were dried over MgSO$_4$, filtered, and concentrated. Chromatography on a 1×18 cm silica gel column, packed with hexane and eluted with 25 mL each of 20% and 30% ethyl acetate/hexane, then 50 mL 50% ethyl acetate/hexane, provided 100 mg clear, colorless oil in 7 mL fractions 8–11.

5-(3E-4-Hydroxy-3-methyl-2-butenyl)-5-allylbarbituric acid

To a solution of the 100 mg dienic barbituric acid prepared according to the immediately preceding Example, in 1 mL dichloromethane, was added 9 mg (84 μmol) selenium dioxide, 6 mg (42 μmol) salicyclic acid, and 0.29 mL (1.09 mmol) of a 3.8M solution of t-butylhydroperoxide in benzene. The solution was stirred well for 12 hr and concentrated. Chromatography on a 1×14 cm column, packed with 30% ethyl acetate/hexane and eluted with 25 mL each of 40%, 50%, 60%, and 70% ethyl acetate/hexane provided 21 mg of the desired product as a clear colorless oil in 7 mL fractions 14–19, as well as a mixture of starting material and an unidentified product in fractions 6–10.

5-{3E-4-[(4'-Fluoresceinyl)methylaminocarbonyloxy]-3-methyl-2-butenyl}-5-allylbarbituric acid This tracer was prepared as described for 5-{3-[(4'-fluoresceinyl)methylaminocarbonyloxy]cyclopent-1-yl}-5-propylbarbituric acid, the tracer of Example 1 above, using as starting material 5 mg of the 5-(3E-4-Hydroxy-3-methyl-2-butenyl)-5-allyl barbituric acid obtained immediately above.

EXAMPLE 6

5-{3E-4-[(4'-Fluoresceinyl)methylaminocarbonyloxy]-3-methyl-2-butenyl}-5-(2-bromoallyl)-barbituric acid The title tracer of this example is illustrated in FIG. 7:

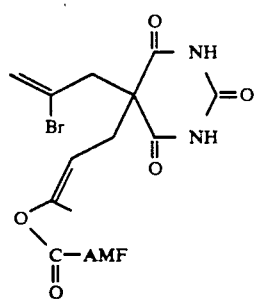

Figure 7

5-(3,3-Dimethylallyl)-5-(2-bromoallyl)barbituric acid

This disubstituted barbiturate was prepared, from 229 mg of 5-(3,3-dimethylallyl)barbituric acid, as described in the previous Example for the preparation of 5-(3,3-dimethylallyl)-5-allylbarbituric acid.

5-(3E-4-Hydroxy-3-methyl-2-butenyl)-5-(2-bromoallyl)barbituric acid

To a solution of 50 mg (0.16 mmol) of the bromide, prepared as described in the immediately preceding paragraph, was added 18 mg (0.16 mmol) selenium dioxide, 0.5 mL absolute ethanol, and 50 μL water. The solution was refluxed for 4 hrs, cooled, and chromatographed directly on a 0.50 mm×20 cm×20 cm plate, using 6% methanol/chloroform to develop. The major band was scraped and eluted with 80% methanol/chloroform to provide 12 mg of a white foam.

5-{3E-4-[(4'-Fluoresceinyl)methylaminocarbonyloxy]-3-methyl-2-butenyl}-5-(2-bromoallyl)-barbituric acid This tracer was prepared, as described for 5-{3-[(4'-fluoresceinyl)methylaminocarbonyloxy]cyclopent-1-yl}-5-propylbarbituric acid, the tracer of Example 1 above, from 4.7 mg of the white foam prepared as described in the immediately preceding paragraph.

EXAMPLE 7

5-<4-{3-[(4'-Fluoresceinyl)methylaminocarbonyloxy]-propyl}cyclopent-2-en-1-yl>-5-(2-methyl)allylbarbituric acid The title tracer of this Example is illustrated in FIG. 8:

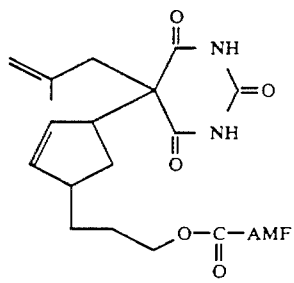

Figure 8

Diethyl cyclopentenylmalonate

To 174 g (2.63 mol) of freshly depolymerized cyclopentadiene, cooled and maintained at −78 C, was added 87.5 g (2.50 mol) gaseous HCl. Meanwhile, 152 mL (1.0 mol) diethyl malonate was added to a solution of 21.4 g (0.93 mol) sodium in 400 mL absolute ethanol. After HCl addition to the cyclopentadiene was complete, the crude yellow chloride, maintained at −78 C, was added in mL portions to the malonate solution. With addition of each 1 ml portion of the malonate solution, considerable heat was produced, the yellow color rapidly dissipated, and copious white precipitate formed. After addition of all of the malonate, the suspension was stirred for 17 hrs, after which most of the ethanol was removed by rotary evaporation, and the reaction was quenched with 200 mL water and extracted 5 ×, each with 100 mL of diethyl ether. The combined extracts were dried over $MgSO_4$, filtered, and concentrated to a clear yellow oil. Distillation of a portion of this material under 0.5 mm Hg pressure yielded 19.091 g clear, light green oil, bp 91–94 C.

Diethyl 1-(4-bromo-cyclopent-2-enyl)malonate

To a solution of 1.0 g (4.42 mmol) of the cyclopentenyl malonate, prepared as described in the immediately preceding paragraph, in 9 mL carbon tetrachloride was added 787 mg (4.42 mmol) N-bromosuccinimide and 5 mg benzoyl peroxide. The solution was heated to reflux to initiate the reaction, and then stirred for 5 mins. It was then refluxed for an additional 30 mins. The suspension was filtered, and the filter cake washed 2 ×, each with 5 mL carbon tetrachloride. Concentration furnished the desired bromide as a clear yellow oil.

Diethyl 4-{1-[3-(2-ethoxy)ethoxypropyl]}cyclopen-2-en-1-yl-malonate

To a cooled (−78 C) solution of 1.390 g (6.63 mmol) 3-(2-ethoxy)ethoxy-1-bromopropane in 3 mL diethyl ether was added 7.8 mL (13.3 mmol) t-butyllithium (1.7M solution in pentane). After stirring 30 mins, 297 mg (3.31 mmol) copper (I) cyanide as a suspension in 1.0 mL diethyl ether was added via cannula. After stirring an additional 30 mins, allowing warming to −50 C and injecting 2 mL tetrahydrofuran, the yellow oil, prepared as described in the immediately preceding paragraph, was added, as a solution in 1 mL tetrahydrofuran, and the resulting solution was warmed to 0 C over 1 hr. The reaction was quenched with saturated $NH_4Cl$ and extracted 4 ×, each with 15 mL ethyl acetate. The extracts were dried over $MgSO_4$, filtered, and concentrated. Chromatography on a 2×18 cm column, packed with hexane and eluted with 50 mL 8% and 50 ml 15% ethyl acetate/hexane, provided 618 mg of a clear colorless oil in 12 mL fractions 8–12.

Diethyl 4-{1-[3-(2-ethoxy)ethoxypropyl]}cyclopen-2-en-1-yl-(2-methyl)allylmalonate To a cooled (0 C) suspension of 18 mg (0.59 mmol) sodium hydride (80% mineral oil dispersion), previously washed 3 ×, each with 5 mL pentane, in 0.2 mL tetrahydrofuran was added 190 mg (0.53 mmol) of the malonate, prepared as in the immediately preceding example, in 0.4 mL dimethylformamide. The solution was warmed slowly to ambient while stirring 30 mins to produce a dark red solution. 73 µL (0.74 mmol) of methallyl chloride and 5 mg sodium iodide were then added, and the resulting mixture stirred for 48 hrs. The reaction was quenched with saturated $NH_4Cl$, acidified to pH 4, and extracted 3 ×, each with 10 mL ethyl acetate. The extracts were dried over $MgSO_4$, filtered, and concentrated. Chromatography on a 1×18 cm column, packed with hexane and eluted with 50 mL 4% and 50 mL 8% ethyl acetate/hexane, provided 55 mg of a clear, colorless oil in 6 mL fractions 6–9.

Diethyl 4-(3-Hydroxypropyl)cyclopent-2-en-1-yl-(2-methyl)allylmalonate

A solution of 109 mg (0.27 mmol) of the ether, prepared as described in the immediately preceding paragraph, in 1.5 mL tetrahydrofuran was treated with 2 drops of 10% aqueous sulfuric acid. After stirring for 30 mins, the reaction was concentrated under a nitrogen stream and chromatographed directly on a 1×16 cm column, packed with hexane and eluted with 25 mL each of 10%, 25%, and 40% ethyl acetate/hexane. From 7 mL fractions 10–12, 79 mg of a clear, colorless oil were obtained.

5-[4-(3-Hydroxypropyl)cyclopent-2-en-1-yl]-5-(2-methyl)allylbarbituric acid The dialkylated barbituric acid was prepared, as described above for the preparation of (3,3-dimethylallyl)barbituric acid from the corresponding diethyl (3,3-dimethylallyl)malonate, using as starting material the 79 mg of diethyl 4-(3-Hydroxypropyl)cyclopent-2-en-1-yl-(2-methyl)allylmalonate derived as described in the immediately preceding example.

5-<4-{3-[(4'-Fluoresceinyl)methylaminocarbonyloxy]-propyl}cyclopent-2-en-1-yl>-5-(2-methyl)allylbarbituric acid This tracer was prepared as described above for 5-{3-[(4'-fluoresceinyl)methylaminocarbonyloxy]cyclopent-1-yl}-5-propylbarbituric acid, the tracer of Example 1 above, using as starting material 5.4 mg of the title compound of the immediately preceding paragraph.

EXAMPLE 8

5-{4-[(4'-Fluoresceinyl)methylaminocarbonyloxy]pent-2-yl}-5-allylbarbituric acid The title tracer of this Example was prepared, following the base-catalyzed amidation described in the final paragraph of Example 1, with 5-[2-(4-chlorocarbonyloxy)pentyl]-5-allylbarbituric acid and 4'-aminomethyfluorescein as starting materials. The preparation of 5-[2-(4-chlorocarbonyloxy)pentyl]-5-allylbarbituric acid, which includes the preferred hapten of the invention, 5-[2-(4-carbonyloxy)pentyl]-5-allyl-barbituric acid, is described in the final paragraph of Example 9.

The title tracer of this Example is illustrated in FIG. 4:

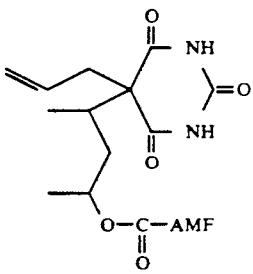

Figure 4

EXAMPLE 9

Preparation of the most preferred immunogen of the invention, 5-[2-(4-carbonyloxy)pentyl]allylbarbituric acid, bovine serum albumin immunogen, illustrated in FIG. 21, is described in the present Example.

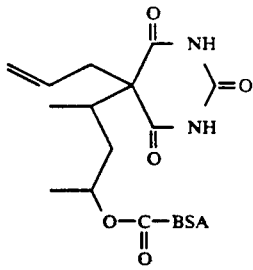

Figure 21

4-(t-Butyldimethylsilyloxy)-2-hydroxypentane

To a solution of 1.00 g (9.60 mmol) 2,4-pentanediol in 9 mL dimethylformamide was added 1.52 g (10.1 mmol) t-butyldimethylsilyl chloride and 915 mg (13.4 mmol) imidazole. The solution was stirred for 12 hrs, diluted in 100 mL of ether, and washed 5 ×, each with 2 mL water. The organic phase was dried over MgSO$_4$, filtered, and concentrated. Chromatography on a 2×18 cm column, packed with hexane and eluted with 100 mL each of 5%, 10%, and 25% ethyl acetate/hexane provided 1.192 g of a clear colorless oil in 10 mL fractions 6-14.

4-(t-Butyldimethylsilyloxy)-2-iodopentane

To a solution of the 1.192 g of the alcohol prepared as described immediately above, 2.01 g (7.65 mmol) triphenylphosphine, and 521 mg (7.65 mmol) imidazole, in 5.5 mL ether and 1.5 mL acetonitrile, was added 1.81 g (7.11 mmol) iodine in portions. The resulting yellow suspension was stirred for 3 hrs and concentrated on a rotary evaporator. The residue was dissolved in dichloromethane, and filtered through a 2×12 cm silica gel column, packed and eluted with 100 mL 20% diethyl ether/hexane. Upon concentration, 1.833 g of a clear, colorless oil was obtained.

Diethyl 2-[4-(t-Butyldimethylsilyloxy)pentyl]malonate

To a cooled (0 C) suspension of 164 mg (5.47 mmol) sodium hydride, previously washed 3 ×, each with 5 mL pentane, in 2 mL dimethylformamide was added 0.84 mL (5.47 mmol) diethyl malonate. After stirring for 1 hr, the 1.833 g of the crude iodide, prepared as described in the immediately preceding paragraph, as a solution in 2 mL tetrahydrofuran, was added, and the reaction warmed to 60 C for 12 hr. The reaction was quenched with water, acidified to pH 4 with 1N HCl, and extracted 3 ×, each with 15 mL ethyl acetate. The combined extracts were dried over MgSO$_4$, filtered, and concentrated. Chromatography on a 2×18 cm silica gel column, packed with hexane and eluted with 50 mL hexane, 100 mL 2%, 100 mL 5%, and 100 mL 10% ethyl acetate/hexane produced 1.612 g of a clear colorless oil from 10 mL fractions 9-18.

Diethyl 2-[4-(t-Butyldimethylsilyloxy)pentyl]allylmalonate

To a suspension of 141 mg (4.70 mmol) sodium hydride (80% mineral oil dispersion), previously washed 3 ×, each with 5 mL pentane, in 5 mL dimethylformamide was added the malonate prepared as described in the immediately preceding paragraph. After stirring for 1 hr, 0.46 mL (5.37 mmol) allyl bromide was added, and the reaction warmed to 60 C for 48 hr. The reaction was quenched with water and extracted 3 ×, each with 15 mL ethyl acetate. The extracts were dried over MgSO$_4$, filtered, and concentrated. Chromatography on a 2×18 cm column, packed with hexane and eluted with 50 mL 1% and 100 mL 5% ethyl acetate/hexane provided 1.635 g clear colorless oil in 10 mL fractions 8-12.

Diethyl 2-(4-Hydroxypentyl)allylmalonate

To a solution, in 0.5 ml tetrahydrofuran, of 185 mg (0.46 mmol) of the malonate, prepared as described in the immediately preceding paragraph, was added 1 0 mL 1.0M tetrabutylammonium fluoride in THF. After stirring for 8 hrs, the solution was concentrated and chromatographed directly on a 1×18 cm column, packed with hexane and eluted with 50 mL each of 5%, 10%, 20%, 50%, and 75% ethyl acetate/hexane 67 mg of a clear colorless oil was obtained from 6 mL fractions 9-18.

5-[2-(4-Hydroxypentyl)]allylbarbituric acid

To a solution of 35 mg (1.52 mmol) sodium in absolute ethanol was added, as a solution in 0.5 mL ethanol, 33 mg (0.55 mmol) urea and 132 mg (0.46 mmol) of the diester, prepared as described in the immediately preceding paragraph. After refluxing for 12 hr, the reaction mixture was concentrated, acidified to pH 3 with 1N HCl, and extracted 3 X, each with 15 mL of ethyl acetate. The extracts were dried over MgSO4, filtered, and concentrated. A portion (49 mg) of this material was applied to a 0.50 mm×20 cm×20 cm plate as a solution in methanol. The plate was developed with 10% methanol/chloroform. Elution of the major band with 80% methanol/chloroform provided 37 mg of a white crystalline solid. This alcohol was used to prepare the immunogen, as described in the immediately following paragraph, as well as the fluoresceinyl tracer described in Example 8 above.

5-[2-(4-Carbonyloxy)pentyl]allylbarbituric acid, bovine serum albumin immunogen

To a cooled (0 C) solution of 35 mg (0.14 mmol) of the alcohol from the immediately preceding paragraph in 1 0 mL tetrahydrofuran was added 1.0 mL of a 12% solution of phosgene in benzene. The resulting solution was stirred for 3 hrs, during which warming to ambient was allowed to occur. Concentration in a stream of dry argon provided 45 mg of a thick, colorless oil. This material was dissolved in 0.77 mL tetrahydrofuran; 70 µL of the solution was used to prepare the tracer in Example 8 (see final paragraph of Example 8), while the remainder was used to make the title immunogen of this paragraph. Thus, with respect to the immunogen, the remainder of the solution was added to a solution of 400 mg bovine serum albumin in 5.6 mL of 0.1M pH 8.0 sodium phosphate buffer and 2.4 mL dimethylformamide. After stirring at ambient for 3 hrs, the reaction mixture was dialyzed over 40 hours 4 times, each against 6 L water. The immunogen solution was frozen until use.

EXAMPLE 10

5-[2-(4-pentenyl)]-5-[1-(2-Carbonyloxy)ethyl]-barbituric acid, bovine serum albumin immunogen The title immunogen of this Example is illustrated in FIG. 17:

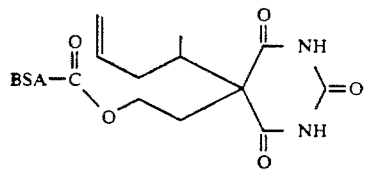

Figure 17

2-Iodo-4-pentene

This iodide was prepared from 5 g 4-hydroxy-1-pentene, according to the procedure described for 4-(t-butyldimethylsilyloxy)-2-iodopentane in Example 9.

Diethyl 2-(4-pentenyl)malonate

This monosubstituted malonate was prepared as described for diethyl 2-[4-(t-butyldimethylsilyloxy)pentyl]malonate in Example 9, starting with the crude iodide obtained as described in the immediately preceding paragraph.

Diethyl 2-(4-pentenyl)-1-(2-tetrahydropyranyloxy)ethylmalonate

To a suspension of 332 mg (2.89 mmol) potassium hydride (35% mineral oil dispersion, which was washed 3 X, each with 5 mL with hexane) in 1 mL tetrahydrofuran and 2 mL dimethylformamide was added 600 mg (2.63 mmol) of the monosubstituted malonate from the immediately preceding paragraph. After stirring for 1 hr, 808 mg (3.16 mmol) of 2-(tetrahydropyranyloxy)-2-iodoethane was added, and the solution stirred for 1 hr at ambient and then refluxed for 12 hrs. The reaction was quenched with water and the mixture extracted 3 X, each with 10 mL ethyl acetate. The extracts were dried over MgSO4, filtered, and concentrated. Chromatography on a 1×18 cm silica gel column, packed with chloroform and eluted with 2% methanol/chloroform, provided 775 mg clear colorless oil in 10 mL fractions 5–8.

5-[2-(4-pentenyl)]-5-[1-(2-Tetrahydropyranyloxy)ethyl]barbituric acid

This barbituric acid derivative was prepared as described for the synthesis of 5-[2-(4-hydroxypentyl)]-allylbarbituric acid in Example 9, using 765 mg of the malonate prepared as described in the immediately preceding paragraph.

5-[2-(4-Pentenyl)]-5-[1-(2-hydroxyethyl)]barbituric acid

To a solution of 140 mg (0.43 mmol) of the tetrahydropyranyl barbituric acid from the immediately preceding paragraph in 2 mL ethanol was added 0 5 mL 5% aqueous sulfuric acid. After refluxing for 20 min, the reaction was concentrated, and chromatographed directly on a 1×10 cm column, packed with chloroform and eluted with 20 mL chloroform, 20 mL 2%, 20 mL 10%, and 20 mL 15% methanol/chloroform, 69 mg white solid was obtained by concentration of 6 mL fractions 9–12.

5-[2-(4-pentenyl)]-5-[1-(2-Carbonyloxy)ethyl]-barbituric acid, bovine serum albumin immunogen The entire amount of the alcoholic precursor from the immediately preceding paragraph was converted, following the final paragraph of Example 9, to the chlorocarbonyloxy derivative and then the title immunogen of this example.

EXAMPLE 11

5-Cyclopentyl-5-[1-(2-Carbonyloxy)ethyl]barbituric acid bovine serum albumin immunogen The title immunogen of this example is illustrated in FIG. 18:

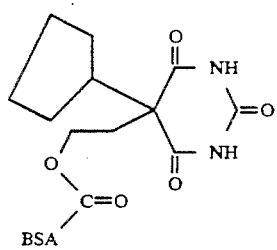

Figure 18

Diethyl cyclopentylmalonate

To a solution of 4.6 g (0.2 mol) sodium in 80 mL absolute ethanol was added 30.4 mL (0.2 mol) diethyl malonate. After briefly stirring, 21.4 mL (0.2 mol) cyclopentyl bromide was added, and the resulting solution refluxed for 12 hrs. Most of the ethanol was then removed by rotary evaporation, and the reaction was quenched with 250 mL of water and extracted 3 X, each with 100 mL ether. The extracts were dried over MgSO4, filtered, and concentrated. Distillation through a 6" Vigreaux at 6 mm Hg provided 32.232 g of a clear colorless oil at bp 122-125 C.

5-Cyclopentylbarbituric acid

To a solution of 3.48 g (151 mmol) sodium in 50 mL absolute ethanol were added 3.02 g (50.4 mmol) urea and 10 g (43.9 mmol) of the malonate prepared in the immediately preceding paragraph. The solution was refluxed overnight, cooled, and concentrated. The reaction was quenched with water, acidified with 10 mL concentrated sulfuric acid, and the resulting white solid collected by filtration of the cooled solution. Recrystallization of the solid from water and then 5% ethanol/water yielded 7.001 g colorless plates with mp 222-223 C.

5-Cyclopentyl-5-(2-tetrahydropyranyloxy)ethylbarbituric acid

The title compound of this paragraph was made as described in Example 10 for diethyl 2-(4-pentenyl)-1-(2-tetrahydropyranyloxy)ethylmalonate, using 860 mg of the crystalline barbituric acid synthesized as described in the immediately preceding paragraph.

5-Cyclopentyl-5-(2-hydroxy)ethylbarbituric acid

This barbituric acid derivative was synthesized from 240 mg of the product obtained from the immediately preceding paragraph, using the procedure for making 5-[2-(4-pentenyl)]-5-[1-(2-hydroxyethyl)]barbituric acid described in Example 10.

5-Cyclopentyl-5-[1-(2-Carbonyloxy)ethyl]barbituric acid bovine serum albumin immunogen Following the procedures described in the final paragraph of Example 9, 43 mg of the alcoholic precursor from the immediately preceding paragraph were converted to the chlorocarbonyloxy derivative which, in turn, was employed to conjugate the hapten to the bovine serum albumin to make the title immunogen of this example.

EXAMPLE 12

5-[4-(1-Carbonyloxy)pentyl]-5-propylbarbituric acid bovine thyroglobulin immunogen 20 mg (78 μmol) of 5-[4-(1-hydroxypentyl)1]-5-propylbarbituric acid, prepared as described in Example 3, were dissolved in 0.5 mL tetrahydrofuran, and 0.5 mL of a 12% solution of phosgene in benzene was added. After stirring for 3 hrs, the solution was concentrated to 28 mg of a white semisolid, which was dissolved in 660 μL dimethylformamide. 300 μL of this solution was added to a solution of 205 mg bovine thyroglobulin in 10 mL of 0.05M sodium phosphate buffer, pH 7.5, for the conjugation. The conjugation reaction mixture was stirred for 2 hrs. at ambient, and dialyzed over 32 hours 4 times, each against 2 L of 0.05M sodium phosphate buffer, pH 7.5. The immunogen solution was frozen until use.

The title immunogen of this Example is illustrated in FIG. 10:

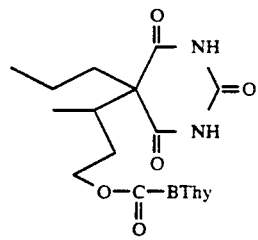

Figure 10

EXAMPLE 13

The FPIA procedure is described in this Example.
A. Reagents
1) Pretreatment solution—A solution containing 0.1M Tris, 1% 5-sulfoxalicylic acid dihydrate, 0.1% copper sulfate pentahydrate, and 0.1% sodium azide (pH 7.5).

2) Tracer—Tracer compound, at approximately 100 nM, in 0.1M pH 6.0 sodium phosphate buffer, containing 20% (v/v) dimethylsulfoxide, 0.01% bovine gamma globulin, and 0.1% sodium azide. Preferred tracer is that of Example 1 (FIG. 1).

3) Antibody—Sheep antiserum raised against an immunogen in accordance with the invention (preferably the immunogen of Example 9, FIG. 21) in a 0.1M pH 6.5 sodium phosphate buffer, containing 1% bovine serum albumin, 2.0% (v/v) ethylene glycol, and 0.1% sodium azide. [The antiserum is obtained by a standard procedure by removing cellular material from blood taken from a sheep that has raised an immune response against the immunogen and then diluting the cell-free antiserum with the above-described buffer to a dilution of about 1:140 (v/v) with the buffer described above in this paragraph (i.e., 7 mL of serum diluted to 1 L with the buffer).

4) Wash solution—A solution containing 50% (v/v) dimethyl sulfoxide in 0.45% sodium chloride, made by mixing 1 volume of dimethylsulfoxide with 1 volume of 0.15M NaCl in water.

5) Calibrators—Pooled normal (i.e., barbiturate-free) human serum preserved with 0.1% sodium azide to which 0.0, 2.0, 5.0, 10.0, 20.0, or 40.0 μg/mL of secobarbital has been added.

6) Controls—Pooled normal human serum preserved with 0.1% sodium azide to which 3.0, 7.5, or 30.0 μg/mL secobarbital has been added.

7) Diluent buffer—A 0.1M pH 7.5 sodium phosphate buffer containing 0.1% sodium azide and 0.01% bovine gamma globulin.

All polarized fluorescence measurements were made using the commercially available ABBOTT LABORATORIES TDx Clinical Analyzer.

B. Assay Protocol
1) 25 μL of an unknown sample or control is pipetted into the predilute well. The pipette is then washed with wash solution before transfer of another sample or control. A sufficient volume of diluent buffer is added to raise the volume in the predilute well to 500 μL. A 6 μL sample from the predilute well and 12.5 μL of pretreatment solution is pipetted into the cuvette. Sufficient dilution buffer is added to raise the volume to 1.0 mL. A background intensity reading is taken.

2) 12.5 μL of pretreatment solution, 25 μL each of tracer and antibody solution, and a 6 μL sample from the predilute well are added to the cuvette. Sufficient diluent buffer is added to raise the final volume to 2.0 mL.

3) The fluorescence polarization due to tracer binding to the antibody (net polarization) is obtained by subtracting the polarized fluorescence intensities of the background from the final polarized fluorescence intensities of the mixture.

4) The polarization values obtained are inversely proportional to the barbiturate concentration of each sample.

5) The net polarization value for a sample is compared to a standard curve prepared using calibrators of known secobarbital content.

The protocol provided above is optimized for barbiturate assay of serum using the TDx system, sheep antiserum raised with the immunogen of formula 21, and tracer of formula 1. Various modifications might be made in the protocol if an assay system different from the TDx, a different antiserum, or a different tracer is employed, or a set of samples anticipated to have an unusually low or an unusually high barbiturate concentration is to be assayed. One such modification might be, for example, to change the volume of diluted sample that is removed from the predilute well into the cuvette. Such modifications are readily within the skill of those of ordinary skill in the FPIA art.

EXAMPLE 14

The present example illustrates performance of the antisera (and, thereby, indirectly, the immunogens) and tracers in accordance with the present invention when employed in the Abbott Laboratories' TDx Analyzer in accordance with the protocol described in Example 13.

Performance can be quantified, using a fixed protocol with an antiserum at a fixed dilution in the system and a tracer at a fixed concentration in the system, in terms of maximum net polarization (in millipolarization units (abbreviated "mP"), with 1000 mP representing complete polarization in the direction of the incident, polarized light and 0 mP representing complete depolarization), span (in mP), and net fluorescence intensity. Maximum net polarization indicates the maximum polarization when a maximum amount of the tracer is bound to the antibody (i.e., using a serum sample that is free of any barbiturates). A maximum net polarization value of over 250 mP is exceptionally good, but a value greater than 230 mP is excellent and acceptable for commercial application. The span indicates the difference between the net polarization with maximum tracer bound to antibody (i.e., no barbiturate present) and the net polarization with minimum tracer bound to antibody (i.e., in terms of the present example, with secobarbital at 40 μg/ml in a serum sample). A larger span makes possible a more accurate, quantitative analysis of data. A span of at least 170 mP is preferred for commercial application. Net fluorescence intensity is a measure of the amplitude of the fluorescence signal that is above background fluorescence; a higher net intensity will give a more accurate measurement. Net fluorescence intensity is the sum of the intensity (above background) of the vertically polarized fluorescence plus twice the intensity (above background) of the horizontally polarized fluorescence (the polarization of the plane-polarized, incident light is defined as "vertical"). For a commercially acceptable anti-barbiturate antiserum/tracer combination, fluorescence intensity in the assay system, with the tracer concentration and antiserum dilution, described above, must be at least three to four times background intensity; at least eight to ten times above background is preferred. Data on performance of antisera (from sheep) and tracers are presented in Table 14.

TABLE 14

| Immunogen for Antiserum | Tracer | Net Polarization mP | Span mP | Net Bkd)[1] | Ratio (NetI/ |
|---|---|---|---|---|---|
| FIG. 21 | FIG. 1 | 257 | 195 | 1674 | 4.7 |
| FIG. 21 | FIG. 2 | 202 | 149 | 1070 | 8.2 |
| FIG. 21 | FIG. 3 | 175 | 131 | 1251 | 10.2 |
| FIG. 21 | FIG. 4 | 238 | 192 | 1156 | 9.6 |
| FIG. 21 | FIG. 5 | 234 | 195 | 3101 | 14.4 |
| FIG. 21 | FIG. 6 | 224 | 192 | 2401 | 8.7 |
| FIG. 21 | FIG. 7 | 195 | 161 | 1295 | 9.3 |
| FIG. 21 | FIG. 8 | 256 | 207 | 1024 | 4.8 |
| FIG. 17 | FIG. 2 | 204 | 118 | 3507 | 30.0 |
| FIG. 18 | FIG. 2 | 193 | 54 | 2400 | 19.6 |
| FIG. 10 | FIG. 2 | 170 | 90 | 1189 | 10.8 |

[1] NetI/Bkd means net intensity divided by background intensity.

EXAMPLE 15

Crossreactivity

The assay of the present invention is a particularly desirable assay for the barbiturates, because it detects members of this class of drugs relatively equivalently and because it fails to detect other substances, such as 1) other narcotic drugs, 2) stimulant drugs, and 3) commonly coadministered drugs, that have posed a problem in immunoassays for barbiturates by cross-reacting with the barbiturates and, consequently, interfering with the assay by resulting in falsely positive, or excessively positive, results.

Crossreactivity was tested for the barbiturates and their metabolites. Compounds were assayed by adding a known quantity of a test compound to drug-free, normal human serum and assaying with the barbiturate assay of the present invention on the Abbott Laboratories TDx Clinical Analyzer (see Example 13) using sheep antiserum to the immunogen of FIG. 21 and the tracer of FIG. 1. Crossreactivity was evaluated by the following formula:

$$\% \text{ Cross reactivity} = 100 \times \frac{\text{Concentration of the Test Compound Found in the Assay}}{\text{Known Concentration of the Test Compound Added}}$$

Representative data are shown in Table 15-1 below.

TABLE 15-1

| Test Compound | Concentration Added (μg/mL) | Concentration Found (μg/mL) | % Cross Reactivity |
|---|---|---|---|
| Allobarbital | 30.0 | 6.42 | 21.4 |
|  | 7.5 | 2.60 | 34.7 |
|  | 3.0 | 1.45 | 48.3 |
| Alphenal | 30.0 | 10.92 | 36.4 |
|  | 7.5 | 4.84 | 64.5 |
|  | 3.0 | 2.73 | 91.0 |
| Amobarbital | 30.0 | 5.48 | 18.3 |
|  | 7.5 | 2.39 | 31.9 |
|  | 3.0 | 1.46 | 48.7 |
| Aprobarbital | 30.0 | 8.21 | 27.4 |
|  | 7.5 | 3.37 | 44.9 |
|  | 3.0 | 1.83 | 61.0 |
| Brallobarbital | 30.0 | 6.90 | 23.0 |
|  | 7.5 | 2.85 | 38.0 |
|  | 3.0 | 1.56 | 52.0 |
| Butabarbital | 30.0 | 7.02 | 23.4 |
|  | 7.5 | 2.86 | 38.1 |
|  | 3.0 | 1.60 | 53.3 |
| Butalbital | 30.0 | 9.33 | 31.1 |
|  | 7.5 | 3.79 | 50.5 |

TABLE 15-1-continued

| Test Compound | Concentration Added (μg/mL) | Concentration Found (μg/mL) | % Cross Reactivity |
|---|---|---|---|
| | 3.0 | 2.06 | 68.7 |
| Butobarbital (Butethal) | 30.0 | 3.93 | 13.1 |
| | 7.5 | 1.91 | 25.5 |
| | 3.0 | 1.08 | 36.0 |
| Cyclobarbital | 30.0 | 4.97 | 16.6 |
| | 7.5 | 2.44 | 32.5 |
| | 3.0 | 1.65 | 55.0 |
| Cyclopentobarbital | 30.0 | 12.83 | 42.8 |
| | 7.5 | 4.80 | 64.0 |
| | 3.0 | 2.21 | 73.7 |
| Pentobarbital | 30.0 | 9.06 | 30.2 |
| | 7.5 | 3.28 | 43.7 |
| | 3.0 | 1.86 | 62.0 |
| Phenobarbital | 30.0 | 4.04 | 13.5 |
| | 7.5 | 2.01 | 26.8 |
| | 3.0 | 1.32 | 44.0 |
| Secobarbital (calibrator) | 30.0 | 30.0 | 100.0 |
| | 7.5 | 7.5 | 100.0 |
| | 3.0 | 3.0 | 100.0 |
| Talbutal | 30.0 | 21.60 | 72.0 |
| | 7.5 | 6.63 | 88.4 |
| | 3.0 | 2.84 | 94.7 |
| Thiamylal | 30.0 | 4.15 | 13.8 |
| | 7.5 | 1.11 | 14.8 |
| | 3.0 | 0.61 | 20.3 |
| Vinyl Barbital | 30.0 | 5.24 | 17.5 |
| | 7.5 | 2.32 | 30.9 |
| | 3.0 | 1.26 | 42.0 |

Cross-reactivity was also tested, by the procedure described above in this Example, for compounds that have structures similar to the barbiturates. Representative data are presented in Tables 15-2 and 15-3. As can be seen by examination of the data in Tables 15-2 and 15-3, the assay system of the present invention has minimal cross-reactivity to many barbiturate-like compounds and other potential interferants in immunoassays for barbiturates.

TABLE 15-2

| Test Compound | Concentration Added (μg/mL) | Concentration Found (μg/ml) | % Cross Reactivity |
|---|---|---|---|
| p-Hydroxyphenytoin | 200 | 0.97 | 0.5 |
| Phenytoin | 200 | 1.05 | 0.5 |
| | 100 | 1.03 | 1.0 |
| | 50 | 0.73 | 1.5 |

TABLE 15-3

| Compound Tested | Conc Tested (μg/mL) |
|---|---|
| Acetaminophen | 1000 |
| Alloxan | 1000 |
| Amitriptyline | 30 |
| Amoxapine | 20 |
| Amphetamine | 100 |
| Caffeine | 1000 |
| Chlorpromazine | 50 |
| Cocaine | 50 |
| Desipramine | 30 |
| Dextromethorphan | 1000 |
| Diazepam | 100 |
| Dyphylline | 1000 |
| Ethchlorvynol | 500 |
| Ethosuximide | 1000 |
| Ethotoin | 1000 |
| Fentanyl | 1 |
| Glutethimide | 200 |
| Ibuprofen | 1000 |
| Mephenytoin | 200 |
| Methaqualone | 500 |
| Methylprylon | 1000 |
| Morphine | 10 |

TABLE 15-3-continued

| Compound Tested | Conc Tested (μg/mL) |
|---|---|
| Phencyclidine | 50 |
| Phenylbutazone | 1000 |
| Primidone | 200 |
| Promethazine | 10 |
| Salicylate | 10,000 |
| 11-Nor-Delta-8-tetrahydrocannabinol-9-carboxylic acid | 10 |
| Theophylline | 1000 |

EXAMPLE 16

Carryover

Employing the wash solution described in Example 13 to rinse the pipette employed in the TDx system to transfer sample into the system, carryover was determined by assaying normal (i.e., barbiturate-free) human serum that had been spiked with 200 μg/ml secobarbital followed, after the wash of the pipette, by barbiturate-free, normal serum. The assay was carried out using sheep antiserum to the immunogen of FIG. 21 and the tracer of FIG. 1 and following the procedure described in Example 13. Carryover was evaluated by the formula:

$$\% \text{ Carryover} = \frac{\text{concentration of secobarbital found in barbiturate-free serum}}{\text{concentration of secobarbital found in secobarbital-containing serum}}$$

% Carryover was found to be less than or equal to a surprisingly small 0.13%.

While the invention has been described with specificity in the instant specification, those of ordinary skill in the art will recognize many modifications and variations of what has been described that fall within the spirit of the invention. It is intended that such variations and modifications be encompassed by the invention as described and claimed.

What we claim is:

1. A compound of Formula I

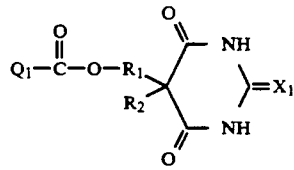

wherein $X_1$ is oxygen or sulfur; $Q_1$ is (a) an activating group for nucleophilic displacement of $Q_1$ by an amino group, (b) an immunogenic polypeptide, suitable as a carrier protein to induce an immune response against a low molecular weight compound, bonded to the carbonyl group through an N-terminal or side-chain amino group of the polypeptide, or (c) a moiety selected from the group consisting of 5-aminofluorescein, 6-aminofluorescein, and a fluorescein corresponding to the formula

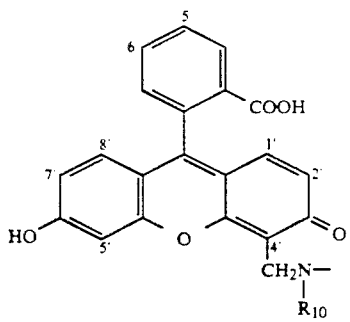

wherein $R_{10}$ is hydrogen, alkyl of 1-6 carbon atoms, or glycl, said moiety bonded to the carbonyl group, to which $Q_1$ is bonded in the compound of Formula I, through the amino group of the moiety; $R_1$ is alkylene of 1 to 8 carbon atoms, cycloalkylene of 3 to 8 carbon atoms, alkenylene of 2 to 8 carbon atoms or cycloalkenylene of 5 to 8 carbon atoms; and $R_2$ is alkyl of 1 to 8 carbon atoms, cycloalkyl of 3 to 8 carbon atoms, alkenyl of 2 to 8 carbon atoms, cycloalkenyl of 5 to 8 carbon atoms, or phenyl provided that (i) $R_1$ is substituted at 0 to 1 carbon atoms, other than the carbon bonded to the oxygen of the carbonyl oxy group, with chloro or bromo, (ii) $R_2$ is substituted at 0 or 1 carbon atom with chloro or bromo, and (iii) if $R_2$ is phenyl, $R_1$ is other than ethylene.

2. A compound of claim 1, wherein $X_1$ is oxygen, $R_1$ is selected from the group consisting of —CH(CH$_3$)CH$_2$(CH$_3$)CH—, —(CH$_2$)$_2$—, —(CH$_2$)$_3$(CH$_3$)CH—, —(CH$_2$)((CH$_3$)C=CH)(CH$_2$)—,

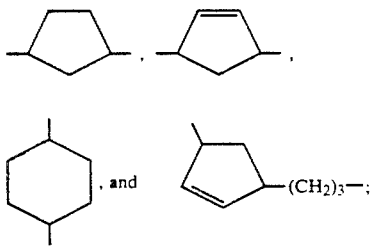

when $R_1$ is —CH(CH$_3$)CH$_2$(CH$_3$)CH—, $R_2$ is —CH$_2$(CH=CH$_2$); when $R_1$ is —(CH$_2$)$_2$—, $R_2$ is cyclopentyl; when $R_1$ is —(CH$_2$)$_3$(CH$_3$)CH—, $R_2$ is selected from the group consisting of n-propyl and allyl; when $R_1$ is cyclopentylene, $R_2$ is n-propyl; when $R_1$ is cyclohexylene, $R_2$ is allyl; when $R_1$ is —CH$_2$((CH$_3$)C=CH)CH$_2$—, $R_2$ is selected from the group consisting of allyl and 2-bromoallyl; when $R_1$ is cyclopentenylene, $R_2$ is 2-methylallyl; and, when $R_1$ is

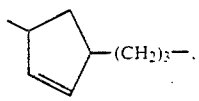

$R_2$ is 2-methylallyl.

3. A compound of claim 2 wherein $Q_1$ is chloro.

4. A compound of claim 3 wherein $R_1$ is selected from the group consisting of —CH(CH$_3$)CH$_2$(CH$_3$)CH— and cyclopentylene.

5. A compound of claim 5 wherein $Q_1$ is selected from the group consisting of 5-aminofluorescein, 6-aminofluorescein, and a fluorescein corresponding to the formula

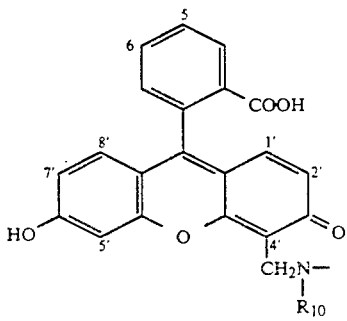

wherein $R_{10}$ is as defined in claim 1.

6. A compound of claim 5 wherein $R_1$ is cyclopentylene.

7. A compound of claim 6 wherein $Q_1$ is 4'-aminofluorescein.

8. A compound of claim 2 wherein $Q_1$ is an immunogenic polypeptide.

9. A compound of claim 8 wherein the polypeptide is selected from the group consisting of keyhole limpet hemocyanin, an avian ovalbumin, a mammalian serum albumin, a mammalian immunoglobulin, a mammalian thryoglobulin, and a polylysine.

10. A compound according to claim 9 wherein the polypeptide is a mammalian serum albumin or a mammalian thryolglobulin.

11. A compound according to claim 10 wherein the polypeptide is bovine serum albumin.

12. A compound according to claim 10 wherein the polypeptide is bovine thryoglobulin.

13. A compound according to claim 11 wherein $R_1$ is —CH(CH$_3$)CH$_2$)CH$_3$)CH—.

14. A compound according to claim 12 wherein $R_1$ is —(CH$_2$)$_3$(CH$_3$)CH—, wherein the methyl-bearing carbon is bonded to the carbon at the 5-position of the barbiturate moiety, and $R_2$ is n-propyl.

* * * * *

UNITED STATES PATENT AND TRADEMARK OFFICE
CERTIFICATE OF CORRECTION

PATENT NO. : 5,099,020
DATED : March 24, 1992
INVENTOR(S) : J. Grote, H. Hu

It is certified that error appears in the above-identified patent and that said Letters Patent is hereby corrected as shown below:

Column 35, line 25, delete "atoms" and insert --atom--, after "0 to 1 carbon".
Column 36, line 12, delete "5" and insert --2--, after "A compound of claim".
Column 36, line 50, delete "-CH($CH_3$)$CH_2$)$CH_3$)CH-." and insert ---CH($CH_3$)$CH_2$($CH_3$)CH-.-- after "$R_1$ is".

Signed and Sealed this

Third Day of August, 1993

Attest:

MICHAEL K. KIRK

*Attesting Officer*   Acting Commissioner of Patents and Trademarks